(12) United States Patent
Rodden et al.

(10) Patent No.: US 12,268,948 B2
(45) Date of Patent: Apr. 8, 2025

(54) EXERCISE MACHINE WITH SCREEN LOCK FUNCTION

(71) Applicant: Nautilus, Inc., Vancouver, WA (US)

(72) Inventors: Steven Michael Rodden, Sherwood, OR (US); Cyrus Evanado, Happy Valley, OR (US); Steve Black, Portland, OR (US); James Taylor, Portland, OR (US); Robert Nicholas Haselmann, Eden Prairie, MN (US)

(73) Assignee: Johnson Health Tech Retail, Inc., Cottage Grove, WI (US)

( * ) Notice: Subject to any disclaimer, the term of this patent is extended or adjusted under 35 U.S.C. 154(b) by 171 days.

(21) Appl. No.: 17/894,928

(22) Filed: Aug. 24, 2022

(65) Prior Publication Data

US 2023/0065979 A1  Mar. 2, 2023

Related U.S. Application Data

(60) Provisional application No. 63/237,042, filed on Aug. 25, 2021.

(51) Int. Cl.
    *A63B 71/06*  (2006.01)
    *A63B 22/02*  (2006.01)
    *A63B 24/00*  (2006.01)

(52) U.S. Cl.
    CPC ........ *A63B 71/0622* (2013.01); *A63B 22/025* (2015.10); *A63B 24/0062* (2013.01);
    (Continued)

(58) Field of Classification Search
    CPC .............. A63B 71/0622; A63B 22/025; A63B 24/0062; A63B 24/0087; A63B 71/0619;
    (Continued)

(56) References Cited

U.S. PATENT DOCUMENTS

| 8,209,743 | B1 * | 6/2012 | Frank | .................. H04L 63/0838 726/28 |
| 2012/0185933 | A1 * | 7/2012 | Belk | .................... H04W 12/126 726/17 |

(Continued)

OTHER PUBLICATIONS

International Search Report received in counterpart PCT Application No. PCT/US2022/041419, mailed Nov. 25, 2022, 5 pages.

(Continued)

*Primary Examiner* — Sundhara M Ganesan
(74) *Attorney, Agent, or Firm* — Klarquist Sparkman, LLP

(57) ABSTRACT

An exercise machine has a lock mode and an unlock mode associated with a screen lock function. A computing device coupled to the exercise machine includes a display, memory, and a processor coupled to the memory. The computing device is configured to detect a user interaction with the computing device or the exercise machine while the exercise machine is in the lock mode, render a screen lock interface on the display in response to the user interaction, receive an input code from the screen lock interface, determine that the input code matches a goal code, and adjust the exercise machine from the lock mode to the unlock mode in response to determining that the input code matches the goal code.

18 Claims, 18 Drawing Sheets

(52) U.S. Cl.
CPC ...... *A63B 24/0087* (2013.01); *A63B 71/0619* (2013.01); *A63B 2071/065* (2013.01); *A63B 2071/0675* (2013.01)

(58) Field of Classification Search
CPC ...... A63B 2071/065; A63B 2071/0675; G16H 20/30; G16H 40/63; H04W 12/06; G06F 21/31; G06F 2221/2133
See application file for complete search history.

(56) References Cited

U.S. PATENT DOCUMENTS

| | | | | |
|---|---|---|---|---|
| 2012/0309314 | A1* | 12/2012 | Chen | H04W 8/005 455/41.2 |
| 2014/0289683 | A1* | 9/2014 | Park | G06F 3/0488 715/863 |
| 2015/0100463 | A1* | 4/2015 | Drazin | G06Q 30/06 705/27.1 |
| 2015/0254464 | A1* | 9/2015 | Shah | G06F 21/46 726/18 |
| 2016/0188870 | A1* | 6/2016 | Sun | H04L 63/06 726/18 |
| 2017/0239525 | A1* | 8/2017 | Kim | A63B 71/0622 |
| 2018/0121035 | A1* | 5/2018 | Filippi | G06F 40/169 |
| 2018/0247065 | A1* | 8/2018 | Rhee | G06F 21/32 |
| 2018/0316802 | A1* | 11/2018 | Takamiya | G06F 3/1205 |
| 2019/0351308 | A1* | 11/2019 | Fima | A63B 24/0087 |
| 2020/0050324 | A1* | 2/2020 | Gavara | H04M 1/67 |
| 2020/0296193 | A1* | 9/2020 | Kim | H04M 1/0274 |
| 2020/0384316 | A1* | 12/2020 | Bestonzo | A63B 22/025 |
| 2021/0264916 | A1* | 8/2021 | Kim | G10L 15/22 |
| 2021/0349619 | A1* | 11/2021 | Crowley | G06F 3/04842 |
| 2022/0239573 | A1* | 7/2022 | Murray | H04W 12/047 |

OTHER PUBLICATIONS

Written Opinion received in counterpart PCT Application No. PCT/US2022/041419, mailed Nov. 25, 2022, 8 pages.

* cited by examiner

EXERCISE MACHINE WITH SCREEN LOCK FUNCTION

CROSS-REFERENCE TO RELATED APPLICATIONS

This application claims the benefit of U.S. Provisional Application No. 63/237,042, filed Aug. 25, 2021, which is incorporated herein by reference in its entirety.

FIELD

The field generally relates to stationary exercise machines and, more specifically, to user interfaces for exercise machines.

BACKGROUND

Various types of stationary exercise machines exist to aid the user in performing physical exercise. An example of a stationary exercise machine that can be found in many fitness gyms and homes is a treadmill that allows a user to walk, run, or climb while staying in the same place. The treadmill typically includes a belt that loops around a stationary deck. In motorized treadmills, the belt loops around in a continuous manner by operation of a motor. Thus, treadmill injury can occur if the treadmill is used in an unsafe manner (e.g., an inactive treadmill that is accidentally started, causing injury to children, pets, or even users who did not expect the treadmill to turn on). Treadmill designers and manufacturers continue to seek safety improvements to the treadmill.

DETAILED DESCRIPTIONS

Example 1— Screen Lock Overview

An exercise machine (e.g., treadmill, stationary bike, elliptical machines, etc.) can have a console with a display for user interaction or can communicate with a portable device (e.g., a mobile phone or tablet) having a display for user interaction. The display can include a touch screen. Alternatively, the user can interact with the display using an input device that is communicatively coupled to the console. A machine application that allows interaction with the exercise machine can run on the console or on the portable device. The machine application can provide a user interface (UI) having one or more windows with various combinations of UI elements that can be manipulated by the user. The UI elements can be linked to various features of the exercise machine and in some cases to multimedia content stored on the console or on servers in the cloud.

In implementations herein, the machine application can provide a screen lock function that when enabled limits interaction with the exercise machine until the user has successfully unlocked the exercise machine. In one example, the screen lock function can present a screen lock view on the display of the console. The screen lock view can include UI elements configured to prompt the user for information to unlock the exercise machine. The requested information can be, for example, a pin code or a combination of user name and password that can be validated by the screen lock function. Successful entry of the information requested by the screen lock function from the user will allow the user to access features of the exercise machine through the machine application UI.

Example 2— Example System Implementing Screen Lock Function

Figure 1:
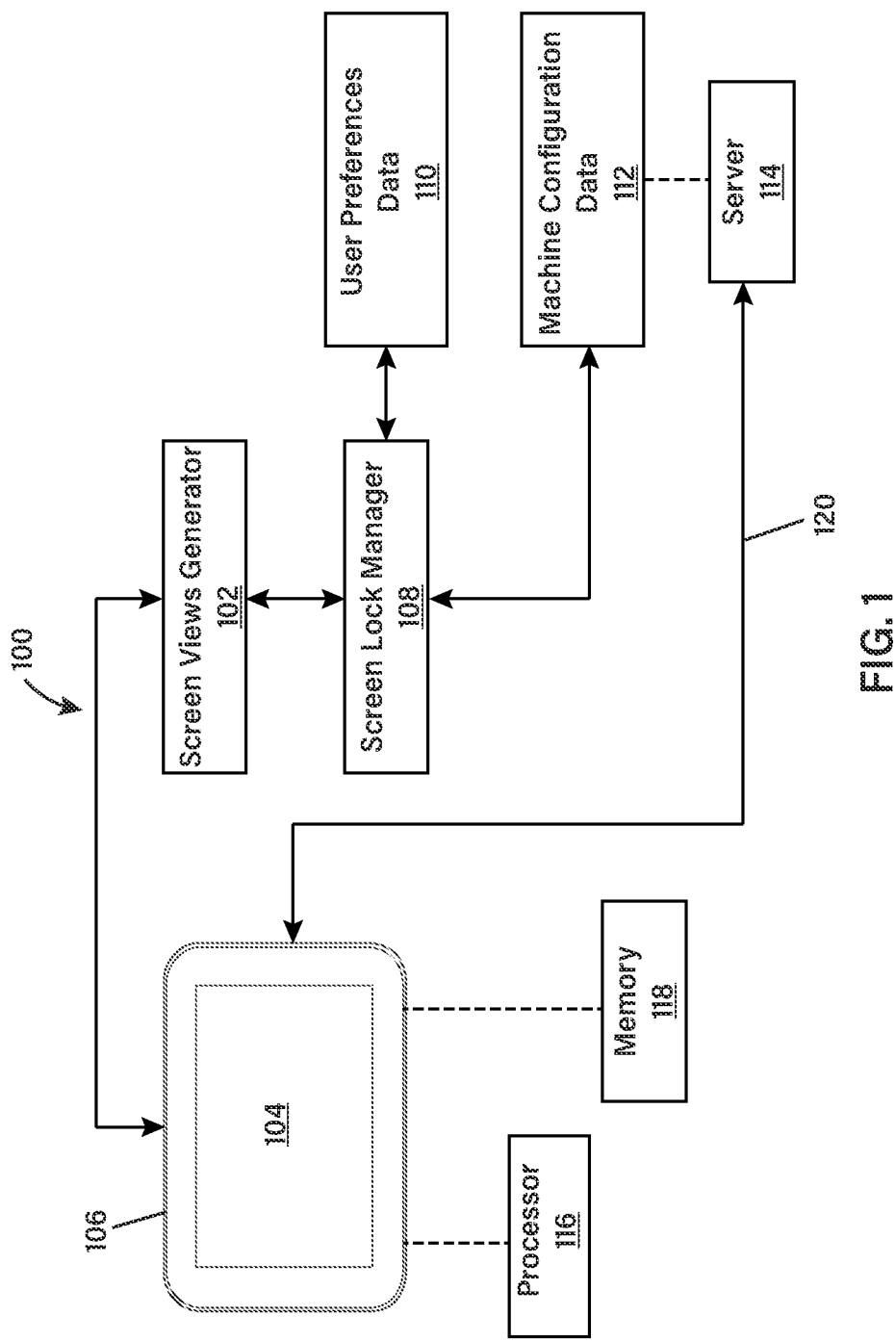
FIG. 1 is a block diagram of a system implementing a screen lock function, according to one example.

FIG. 1 illustrates an example system 100 implementing a screen lock function. In the example, the system 100 can include a screen views generator 102 that generates one or more screen views and presents the screen views on a display 104 of a computing device 106. The computing device 106 can be a console of an exercise machine or a portable device communicatively coupled to an exercise machine (e.g., a portable device connected to a console of an exercise machine over a Bluetooth connection). The screen views generator 102 can detect user interaction with the screen views presented on the display 104.

The system 100 can include a screen lock manager 108 that determines which screen view the screen views generator 102 should generate and present on the display 104. The screen lock manager 108 can receive information about user interaction with the screen views on the display 104 from the screen views generator 102.

The system 100 can include user preferences data 110, which can include a record of user preferences related to the screen lock function along with other information. The system 100 can include machine configuration data 112, which can include a record of screen lock configurations for the exercise machine along with other information.

The computing device 106, such as an Android tablet or phone, includes a processor 116 and memory 118 to execute instructions of the machine application. The screen views generator 102, screen lock manager 108, and user preferences data 110 can be part of the machine application running in the computing device 106. The machine configuration data 112 can be stored on a server 114, which can be in a cloud, for example. The computing device 106 can include features to communicate with the server 114 over a communication link 120. The computing device 106 can include additional features to allow the user to consume multimedia content (e.g., audio and video content) as well as receive information from sensors (e.g., heart rate sensor) on the exercise machine.

Example 3— Example Method Implementing First Time Use of Screen Lock Function

Figure 2:
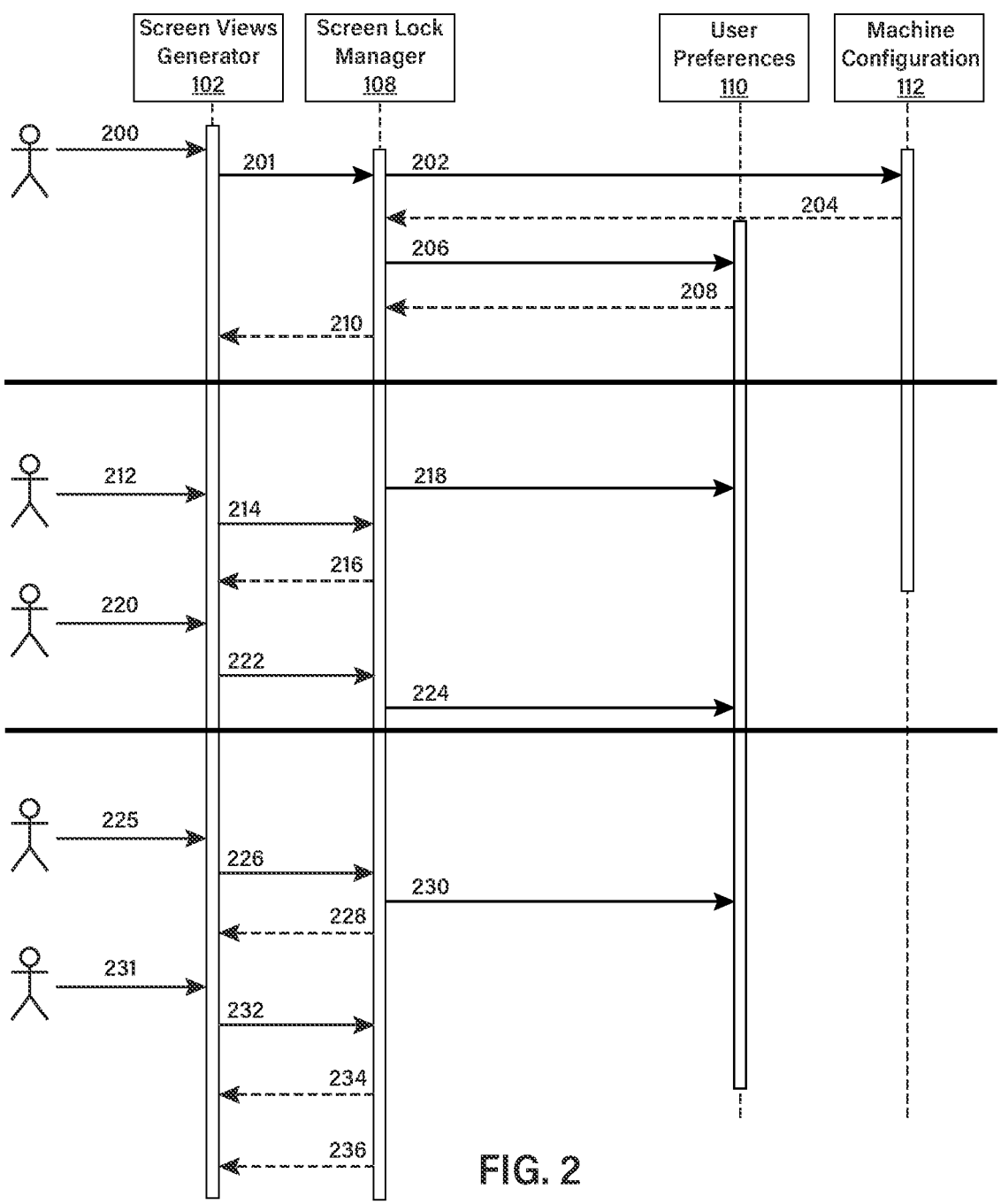
FIG. 2 is a sequence diagram illustrating first time use of a screen lock function of an exercise machine, according to one example.
Figure 11:
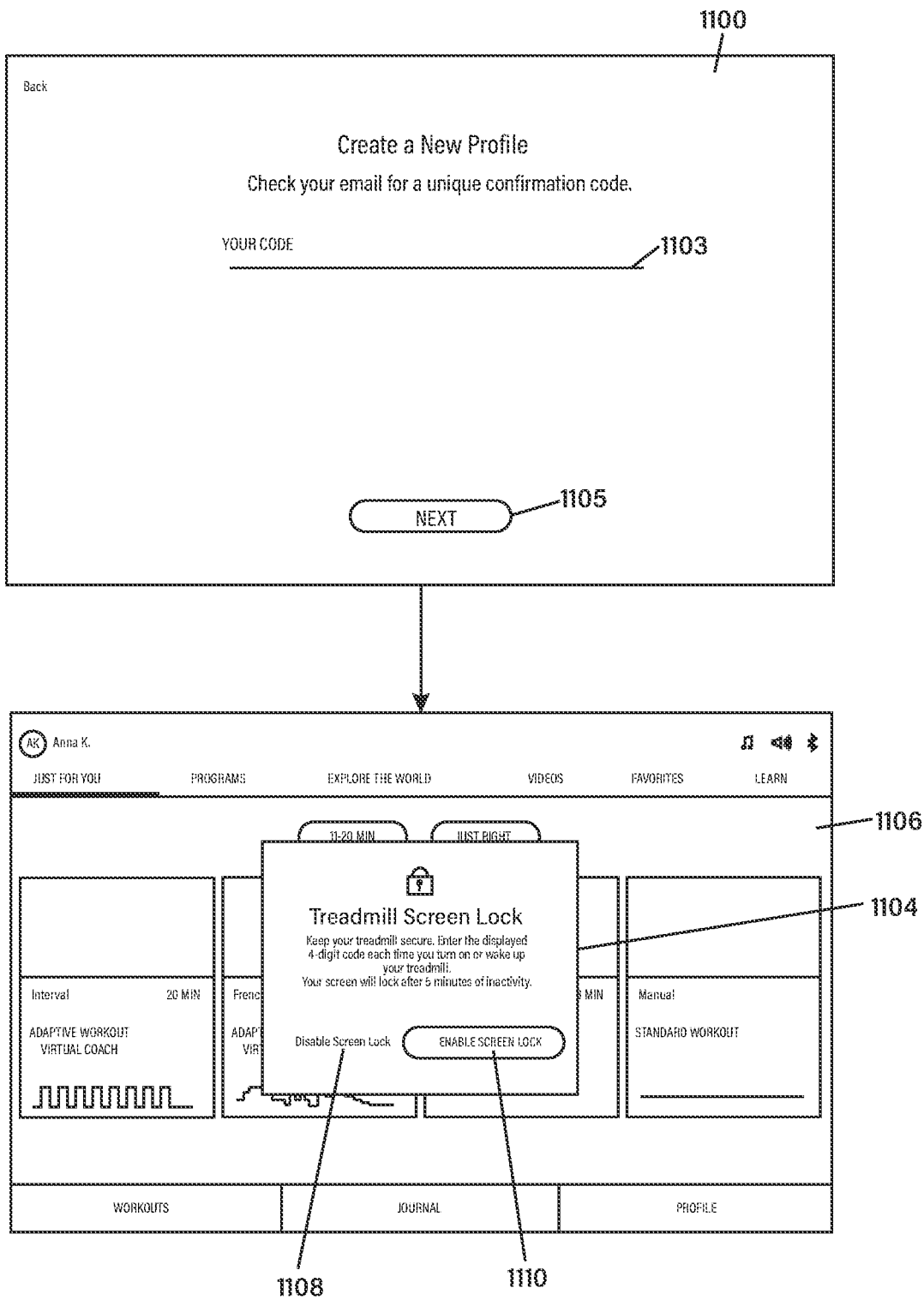
FIG. 11 is a schematic illustration of an example of registering a new user on an exercise machine with a screen lock function.
Figure 12A:
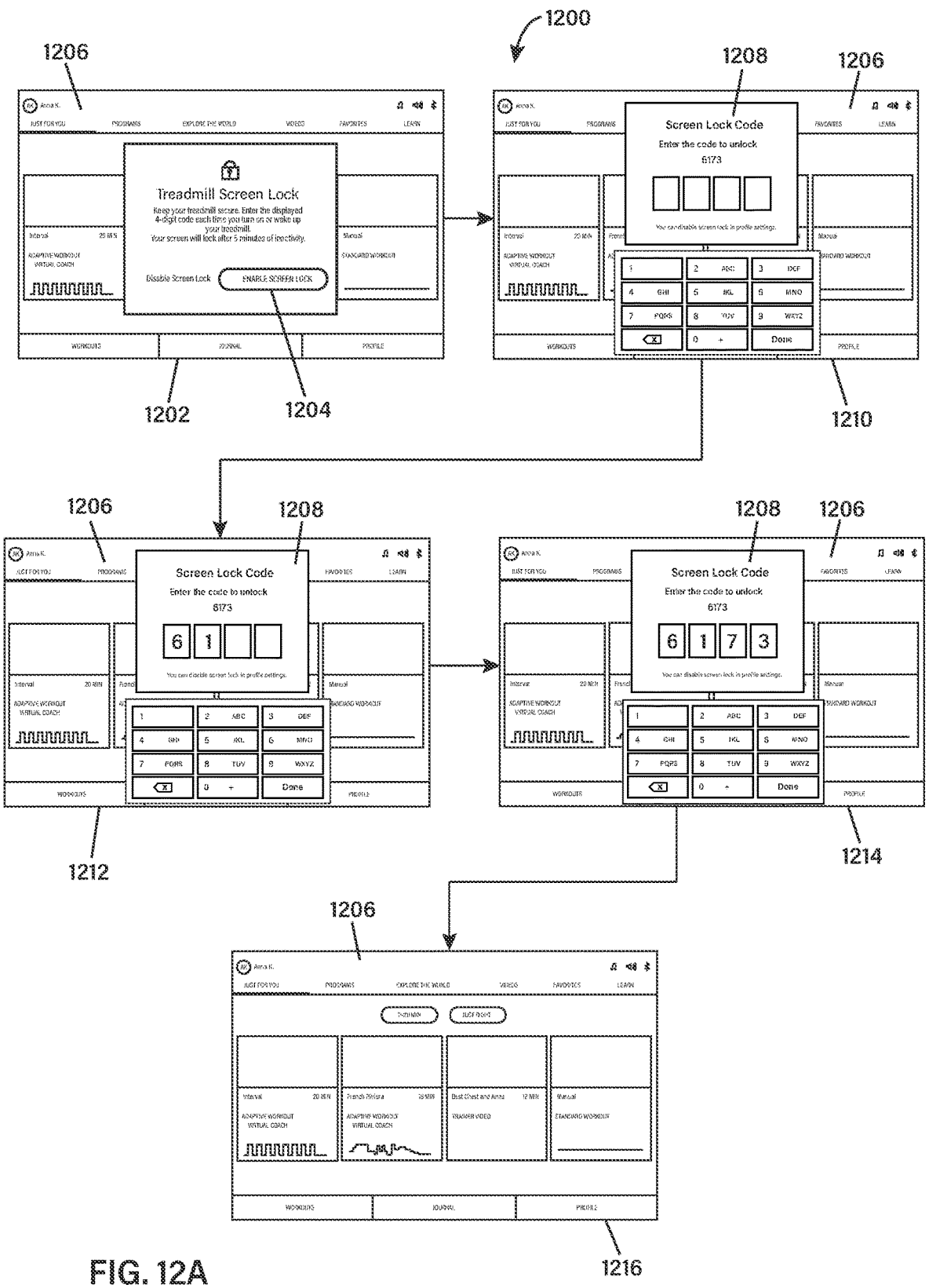
FIG. 12A is a schematic illustration of an example of accessing a training screen of a machine application user interface with a screen lock function.
Figure 12B:
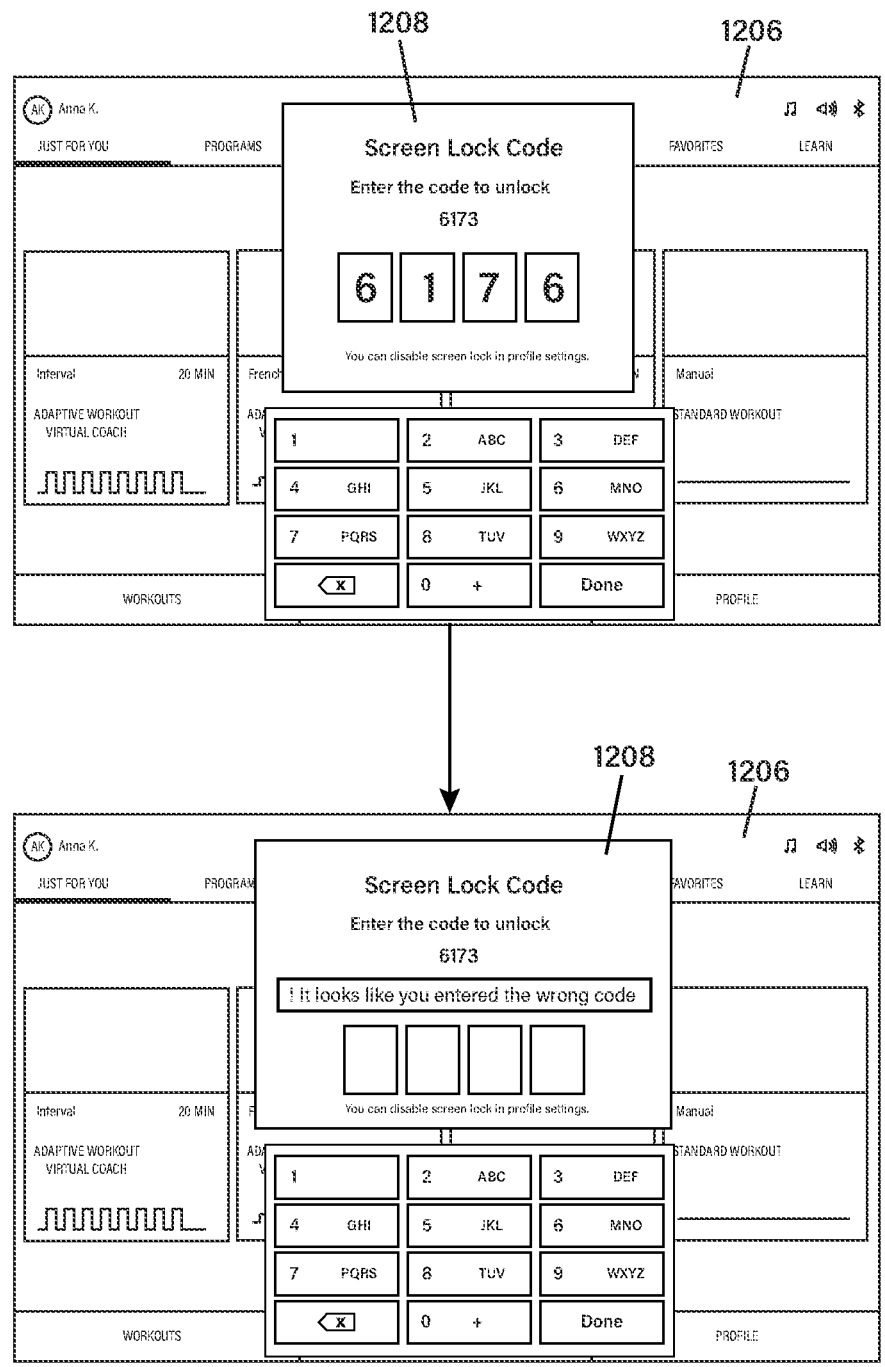
FIG. 12B illustrates an error state when a user enters a wrong code on a screen lock view.
Figure 13:
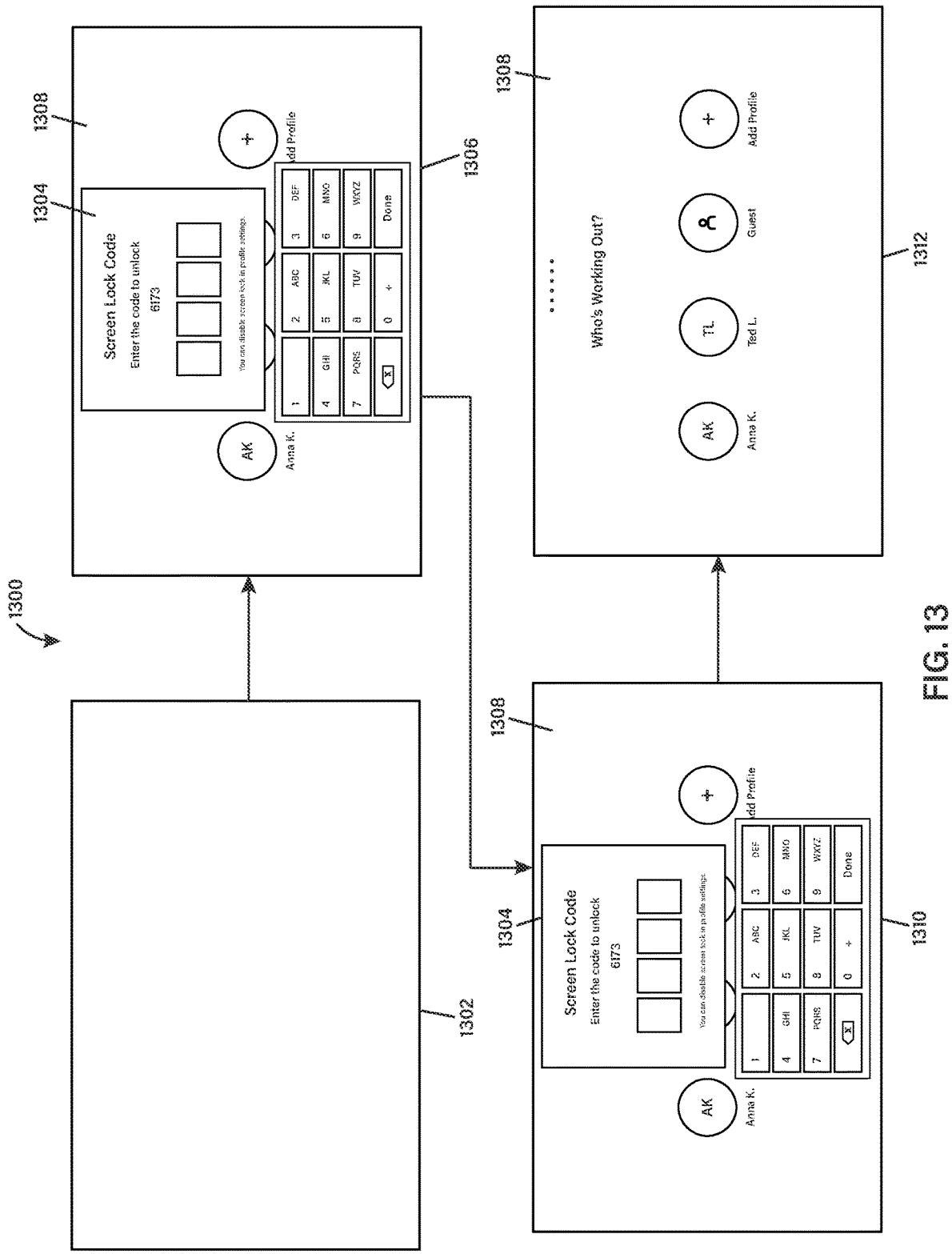
FIG. 13 is a schematic illustration of an example of accessing a home screen of a machine application user interface with a screen lock function.

FIG. 2 is a sequence diagram illustrating first time use of a screen lock function of an exercise machine (also, see FIGS. 11-13). The user taps a screen of the display 104 (see Example 2) while the exercise machine is in a locked mode (e.g., a motor coupled to a movable element of the exercise machine is not in an enabled state or is not running). The screen views generator 102 (see Example 2) detects 200 the tapping and informs 201 the screen lock manager 108 (see Example 2) that a user has tapped the screen. The screen lock manager 108 sends 202 a request to the server for the machine configuration data 112. The screen lock manager 108 receives the machine configuration data 112 and determines whether the screen lock function has been enabled for the exercise machine.

Figure 6:
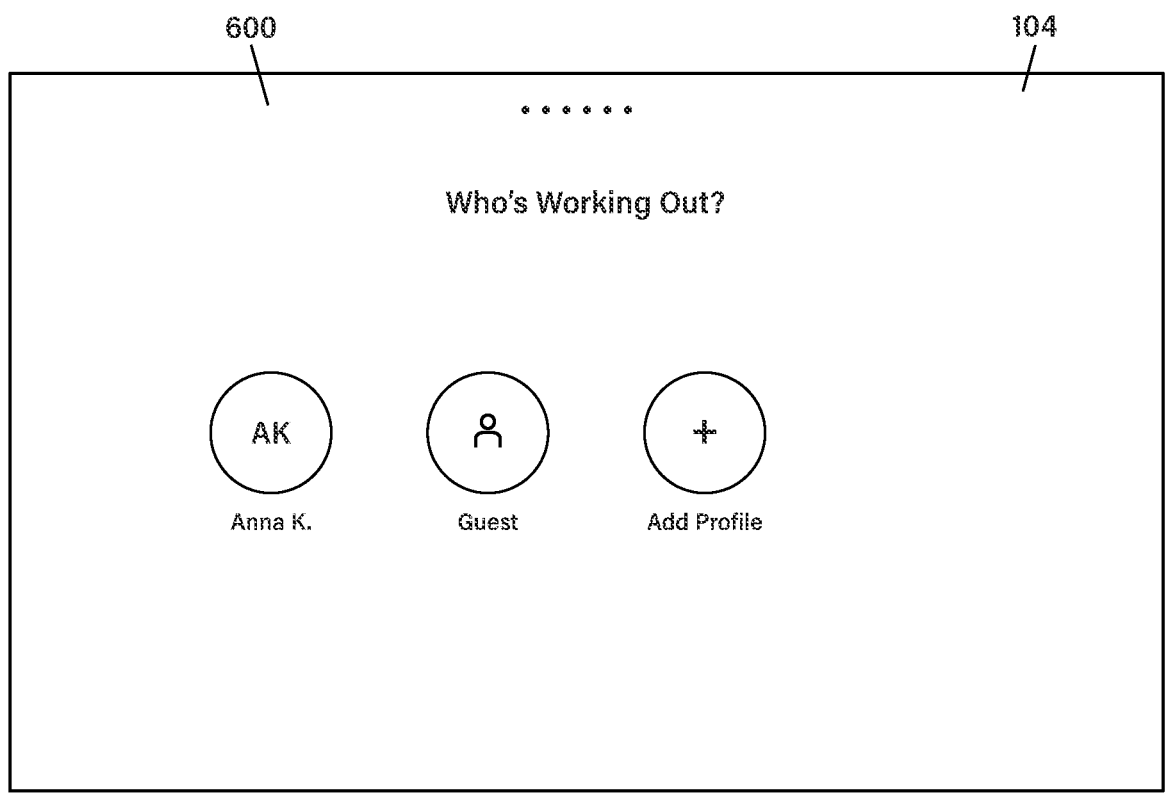
FIG. 6 is a schematic illustration of an example home screen view of a graphical user interface of a machine application.

In some examples, when the user first taps the screen of the display 104, a home screen view of the machine application UI can be presented on the display 104 by the screen views generator 102. The home screen view can show the user profiles registered on the exercise machine. The user can tap on an appropriate user profile or select an option to add a user profile. An example of a home screen view is illustrated in FIG. 6. For the purposes of Example 3, it is assumed that the user is registered on the machine and can simply tap the appropriate user profile. The screen lock manager 108 can determine a user identifier based on the user profile the user taps on.

In some examples, instead of the screen views generator 102 detecting tapping on the screen of the display 104 (as indicated at 200), the screen views generator 102 can detect a different type of user interaction with the exercise machine. For example, the exercise machine can have a load cell that detects when a user is on a movable element (or motorized element) of the exercise machine. The screen views generator 102 can receive load measurements from the load cell. When the screen views generator 102 receives a load measurement that indicates that a user is on the exercise machine (e.g., a load measurement that exceeds a predetermined threshold) while the exercise machine is in the locked mode, the screen views generator 102 can inform the screen lock manager 108 that a user is on the exercise machine. The screen lock manager 108 can then send 202 the request for the machine configuration data 112 and determine whether the screen lock function has been enabled for the exercise machine.

The screen lock manager 108 can send a request 206 for the user preferences data 110. The screen lock manager 108 receives 208 the user preferences data 110. In cases where a user identifier is available (e.g., by detecting the user identifier associated with a user profile tapped on the home screen view), the request 206 can include the user identifier so that only the relevant portion of the user preferences data 110 is received by the screen lock manager 108, or the screen lock manager 108 can receive the user preferences data 110 associated with all the users registered on the exercise machine and then extract the relevant portion of the user preferences data 110 based on the user identifier.

The screen lock manager 108 determines whether the user has reviewed the screen lock function from the user preferences data 110. In Example 3, it is assumed that the user has not reviewed the screen lock function. Therefore, the screen lock manager 108 requests 210 the screen views generator 102 to present a screen lock authorization view to the user on the display 104 (see Example 2).

In some examples, the screen lock manager 108 can request the screen views generator 102 to present the screen lock authorization view to the user on the display 104 based only on determining from the machine configuration data 112 that the screen lock function is enabled on the exercise machine (see Example 15). This option can be used when user identifier information is not accessible or the screen lock function is set globally for all users registered on the exercise machine.

Figure 3:
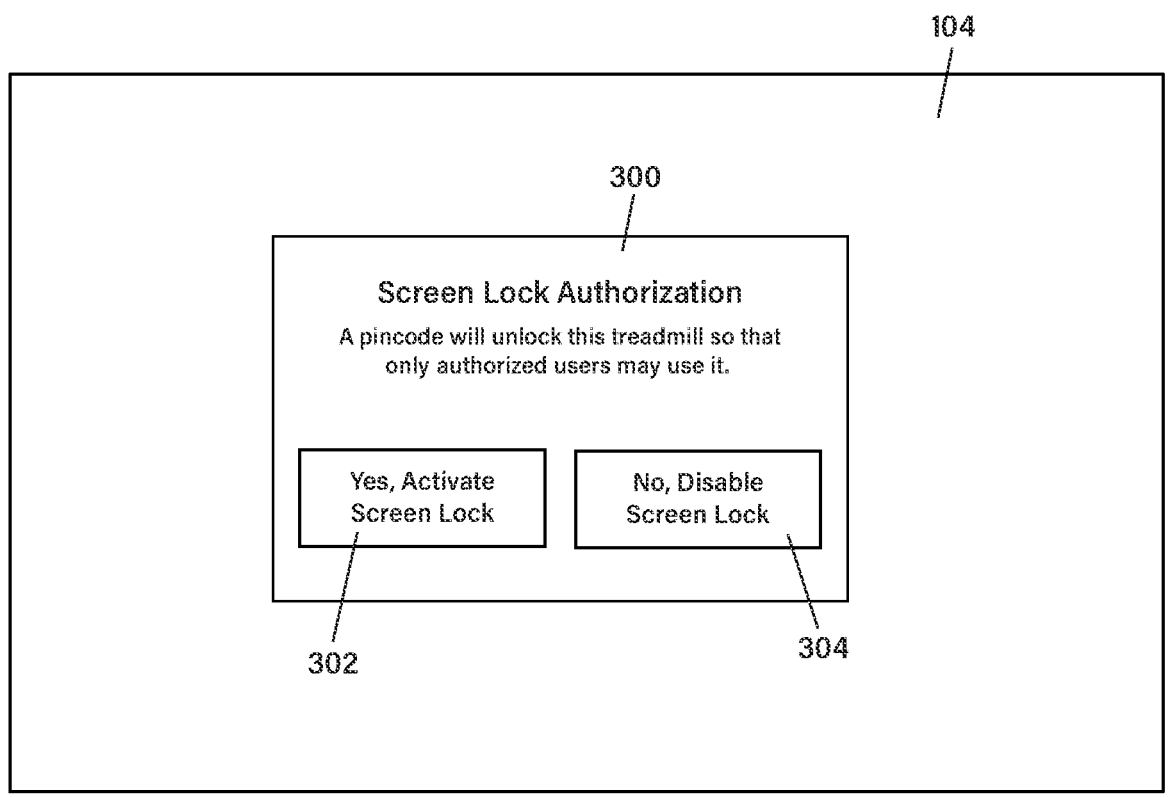
FIG. 3 is a schematic illustration of an example screen lock authorization view.

FIG. 3 shows an example of a screen lock authorization view 300. In the example, the screen lock authorization view 300 includes a first button 302 that the user can select to accept use of the screen lock function on the exercise machine and a second button 304 that the user can select to decline use of the screen lock function on the exercise machine.

Example 4— Example Method Implementing Declining Screen Lock Function

In Example 4, it is assumed that the user selects the option to decline use of the screen lock function from the screen lock authorization view 300 (e.g., selects button 304 in FIG. 3). In one example, the user selection to decline use of the screen lock function applies to all users of the exercise machine. As described in Examples 7 and 8, a user of the machine can have an opportunity to enable or disable the screen lock function through the profile settings for the exercise machine.

Returning to FIG. 2, the screen views generator 102 detects 212 that the user has declined to use the screen lock function. The screen lock manager 108 receives 214 the selection of the user from the screen views generator 102 and requests 216 the screen views generator 102 to confirm the decision of the user. The screen lock manager 108 also updates 218 the user preferences data 110 to include information that the user has reviewed the screen lock function.

Figure 4:
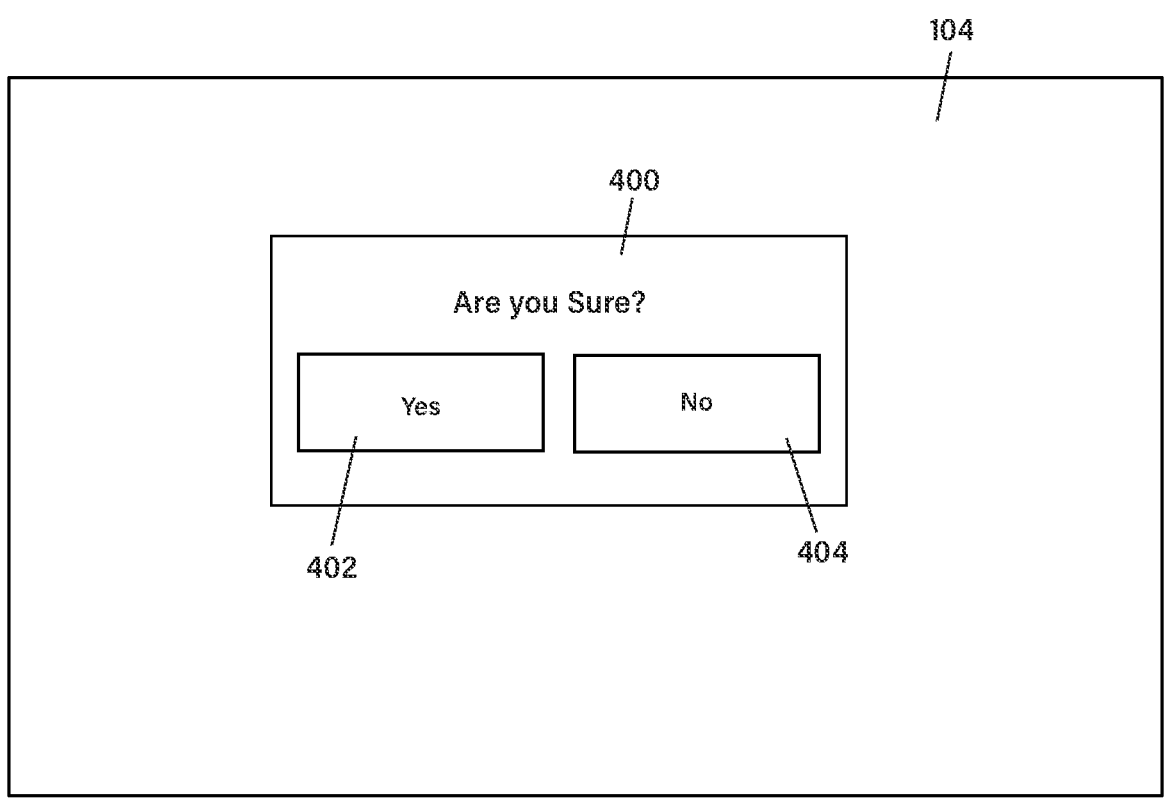
FIG. 4 is a schematic illustration of an example confirmation view for the screen lock authorization view of FIG. 3.

FIG. 4 shows an example of the confirmation view 400. In the example, the confirmation view 400 includes a first button 402 that the user can select to confirm that the user accepts the screen lock function and a second button 404 that the user can select to confirm that the user declines the screen lock function. In Example 4, the user confirms that the screen lock function is declined (e.g., by selecting button 404).

Returning to FIG. 2, the screen views generator 102 detects 220 that the user has confirmed that the screen lock function is declined. The screen lock manager 108 receives 222 the selection of the user from the screen views generator 102. The screen lock manager 108 then updates 224 the user preferences data 110 with the information that the user has declined to use the screen lock function.

Example 5— Example Method Implementing Accepting Screen Lock Function

In Example 5, it is assumed that the user selects the option to accept use of the screen lock function from the screen lock authorization view 300 (see Example 3). Referring to FIG. 2, the screen views generator 102 detects 225 that the user has selected the option to accept use of the screen lock function. The screen lock manager 108 receives 226 the selection of the user from the screen views generator 102 and requests 228 the screen views generator 102 to generate a screen lock view with a pin code and present the screen lock view to the user. The screen lock manager 102 also updates 230 the user preferences data 110 to include information that the user has accepted to use the screen lock function.

Figure 5A:
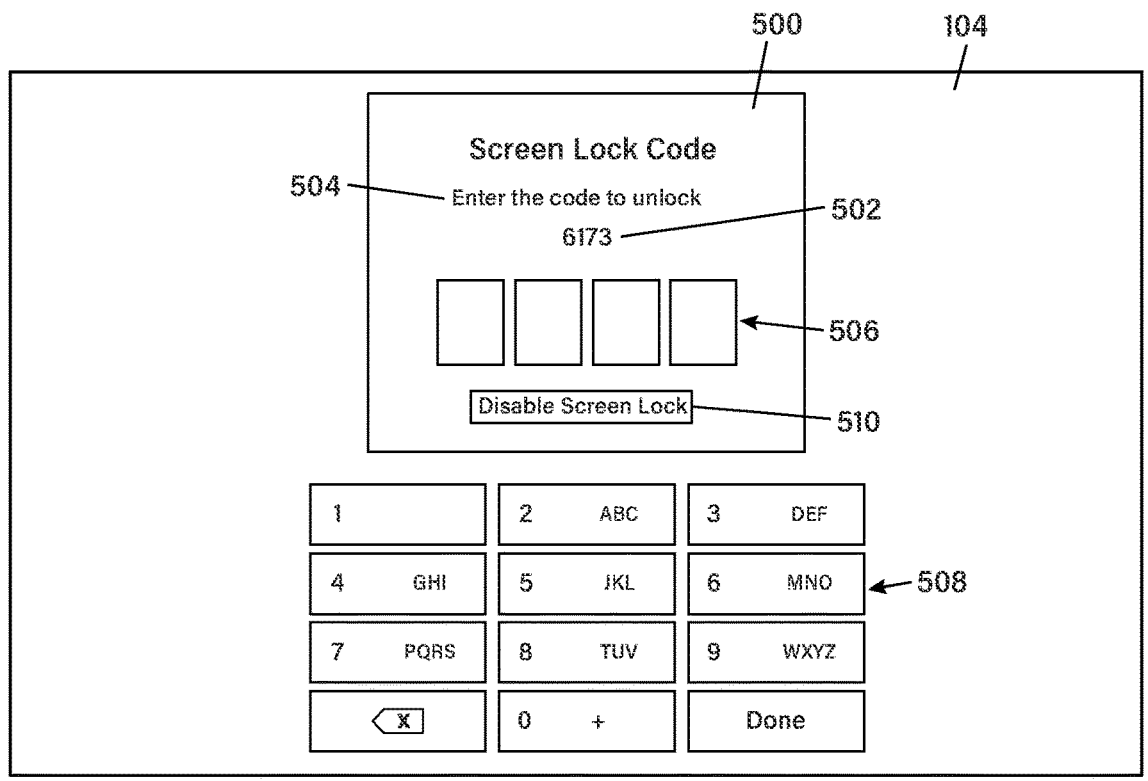
FIG. 5A is a schematic illustration of an example screen lock view with a goal code.
Figure 5B:
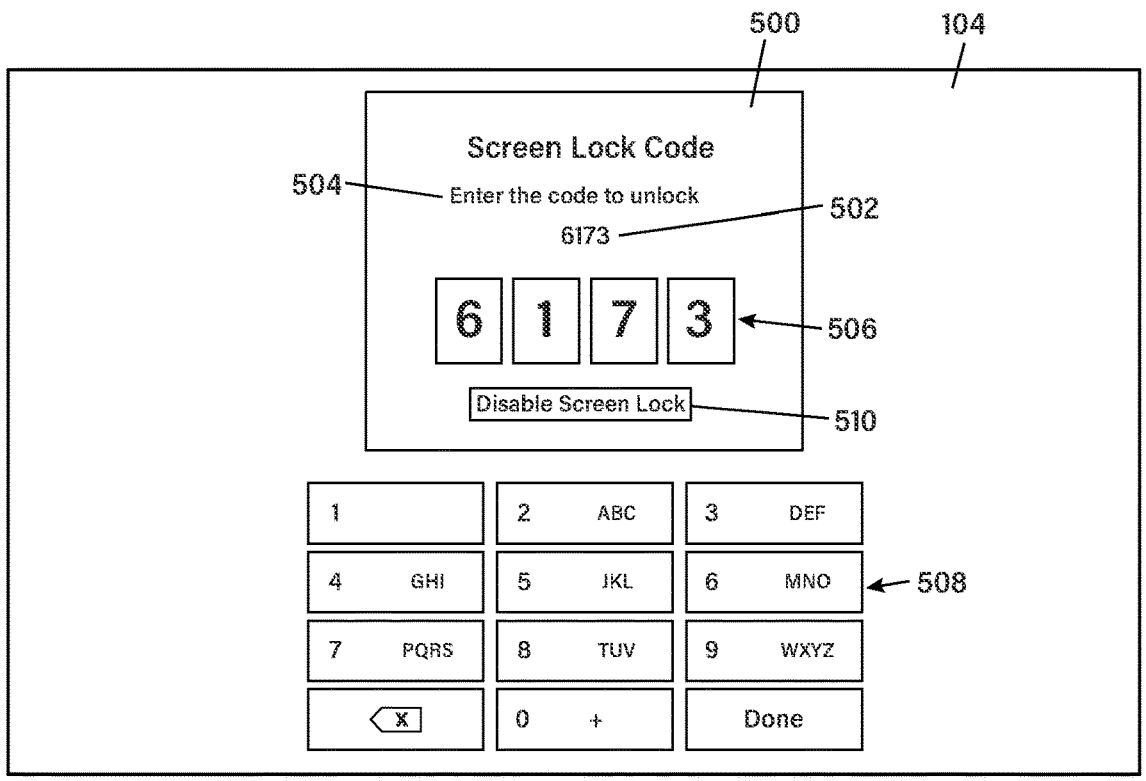
FIG. 5B illustrates the screen lock view of FIG. 5A with user input code, according to one example.

FIG. 5A illustrates an example of a screen lock view 500 (also, see FIGS. 11-13). In the example, the screen lock view 500 includes a pin code 502 (which can also be referred to as "goal code" herein) and text prompt 504 for the user to enter the pin code. In one implementation, the value of the pin code 502 displayed with the screen lock view 500 is automatically randomly generated by the screen lock manager 108 and provided to the screen views generator 102 with the request 228 to generate the screen lock view 500. For illustrative purposes, the pin code 502 is shown as having the value "6173". The user can enter the value of the pin code 502 in the text boxes 506 (or cells) of the screen lock view 500 using a virtual keypad 508 presented on the screen of the display 104 (see Example 2), as illustrated in FIG. 5B.

Returning to FIG. 2, in one example, after the user selects the "Done" key (or an equivalent submission key) in the keypad 508 (shown in FIG. 5B), the screen views generator 102 detects 231 the code entered by the user. In some examples, the code entered by the user can be automatically submitted after the user has entered an expected number of digits based on the number of digits in the displayed pin code 502 (see FIG. 5B), and the screen views generator 102 can detect 231 the code entered by the user. The screen lock manager 108 receives 232 the code from the screen views generator 102 and compares the code entered by the user to the pin code 502 displayed on the screen lock view 500 (see FIG. 5B). If the code entered by the user matches the displayed value of the pin code 502, the screen lock manager 108 requests 234 the screen views generator 102 to generate a home screen view and present the home screen view to the user. The display is unlocked when the home screen view is presented. FIG. 6 shows an example of a home screen view 600 that can be presented to the user. Through the home screen view 600, the user can access the machine application UI and features of the exercise machine.

Returning to FIG. 2, if the code entered by the user does not match the pin code displayed on the screen lock view 500 (see FIG. 5B), the screen lock manager 108 can request 236 the screen views generator 102 to display a re-prompt for a valid pin code to the user (also, see FIG. 12B). The user can enter another code in the text boxes 506 of the screen lock view 500 using the keypad 508. The sequence of actions 231, 232, 234, 236 can be repeated until the user has provided a valid pin code. The request 236 to display a re-prompt for a valid pin code can in some cases include a new pin code randomly generated by the screen lock manager 108 and transmitted to the screen views generator 102, which can refresh the screen lock view with the new pin code (also, see FIG. 12B).

Example 6— Example Method Implementing Subsequent Use of Screen Lock Function

Figure 7:
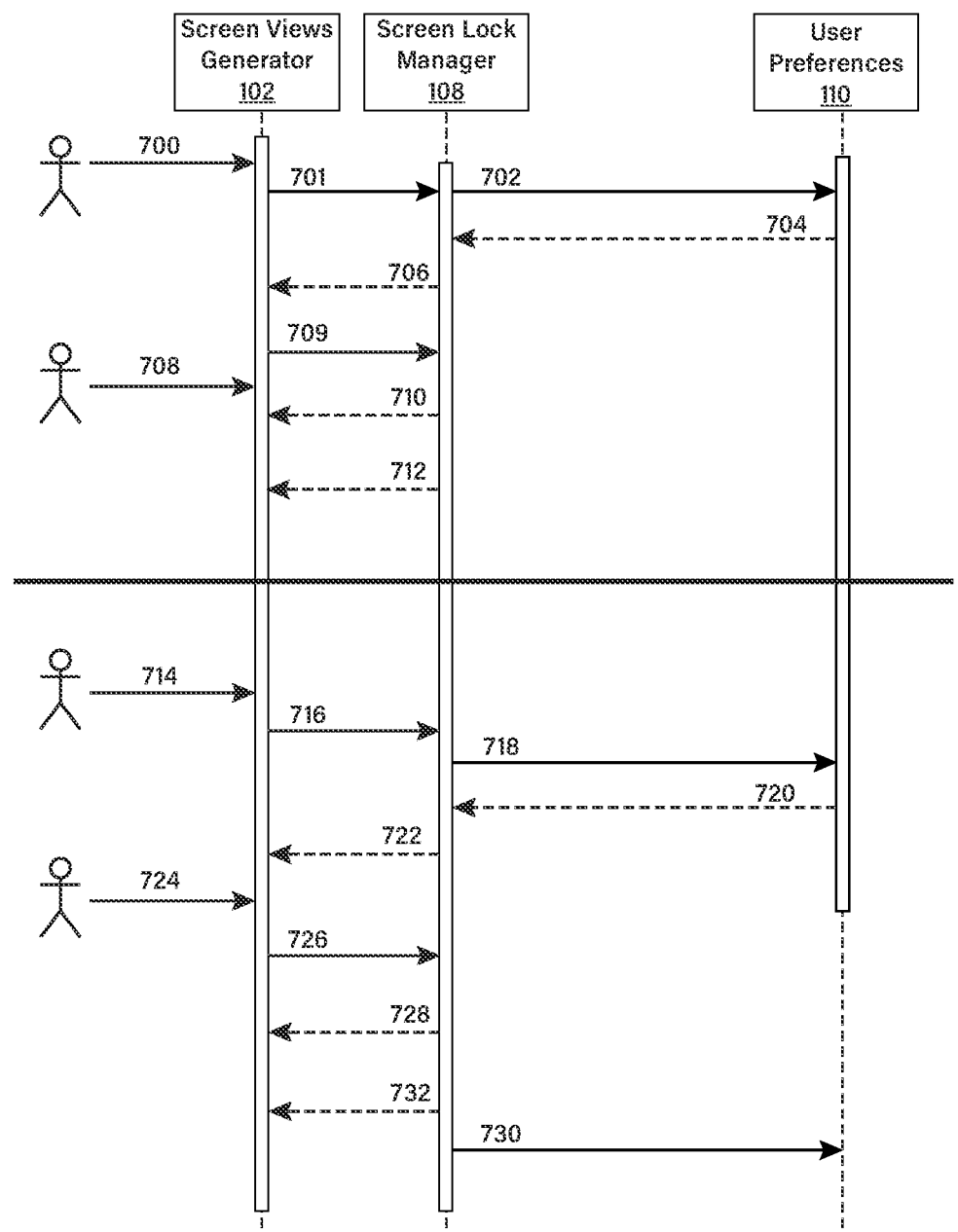
FIG. 7 is a sequence diagram illustrating subsequent use of a screen lock function of an exercise machine, according to one example.

FIG. 7 is a sequence diagram illustrating subsequent use of the screen lock function of the exercise machine (also, see FIGS. 11-13). The user taps the screen of the display 104 (see Example 2). The exercise machine wakes up. The screen views generator 102 detects 700 the tapping and informs 701 the screen lock manager 108 that a user has tapped the screen. The screen lock manager 108 sends a request 702 for the user preferences data 110. The screen lock manager 108 receives 704 the user preferences data 110 and determines from the data if the user has enabled the screen lock function. In Example 6, it is assumed that the user has enabled the screen lock function.

The screen lock manager 108 sends a request 706 to the screen views generator 102 to generate a screen lock view with a pin code and present the screen lock view to the user (see Example 5). The screen views generator 102 detects 708 a code entered in the screen lock view. The screen lock manager 108 receives 709 the code entered by the user from the screen views generator 102 and compares the code to the pin code used in generating the screen lock view. If the code entered by the user matches the pin code, the screen lock manager 108 sends a request 710 to the screen views generator 102 to display the home screen view of the exercise machine. On the other hand, if the code entered by the user does not match the pin code, the screen lock manager 108 sends a request 712 to the screen views generator 102 to re-prompt the user for a valid pin code (see Example 5).

Example 7— Example Method Implementing Subsequent Deactivation of Screen Lock Function After presenting the screen lock view to the user (e.g., in response to request 710 in Example 6), the user may want to disable the screen lock function. FIG. 5A shows that the screen lock view 500 can include a button 510 to disable the screen lock function. Therefore, instead of the user entering a pin code in the screen lock view 500 (as in Example 6), the user can select the button 510 to disable the screen lock function.

Returning to FIG. 7, the screen views generator 102 detects 714 selection of the button 510. The screen lock manager 108 receives 716 the request of the user to disable the screen lock function from the screen views generator 102. The screen lock manager requests 718 the user preferences data 110. The screen lock manager receives 720 the user preferences data 110 and determines if the user has enabled the screen lock function.

In Example 6, it is assumed that the user has enabled the screen lock function. Therefore, the screen lock manager 108 requests 722 the screen views generator 102 to prompt the user for the pin code displayed on the screen lock view.

The screen views generator 102 detects 724 the code entered by the user. The screen lock manager 108 receives 726 the code entered by the user and compares the code to the pin code used in generating the screen lock view. If the code entered by the user matches the pin code, the screen lock manager 108 requests 728 the screen views generator 102 to display the home screen view of the exercise machine. The screen lock manager 108 also updates 730 the user preferences data 110 with information that the screen lock function for the user has been disabled. If the code entered by the user does not match the pin code, the screen lock manager 108 sends a request 732 to the screen views generator 102 to re-prompt the user for a valid pin code.

Figure 8:
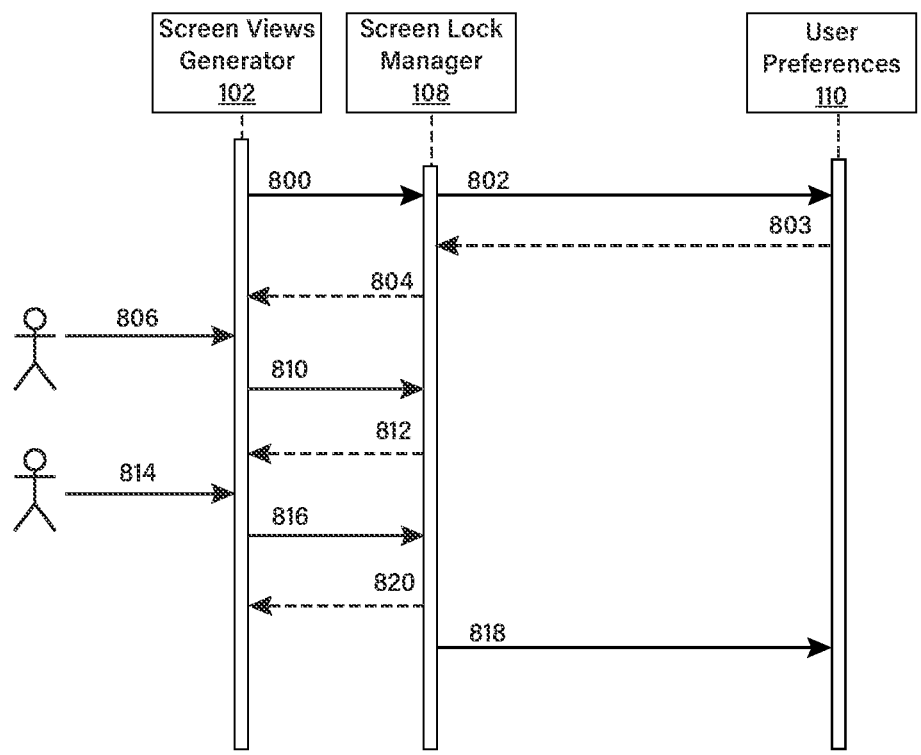
FIG. 8 is a sequence diagram illustrating enabling a screen lock function of an exercise machine from profile settings, according to one example.
Figure 15:
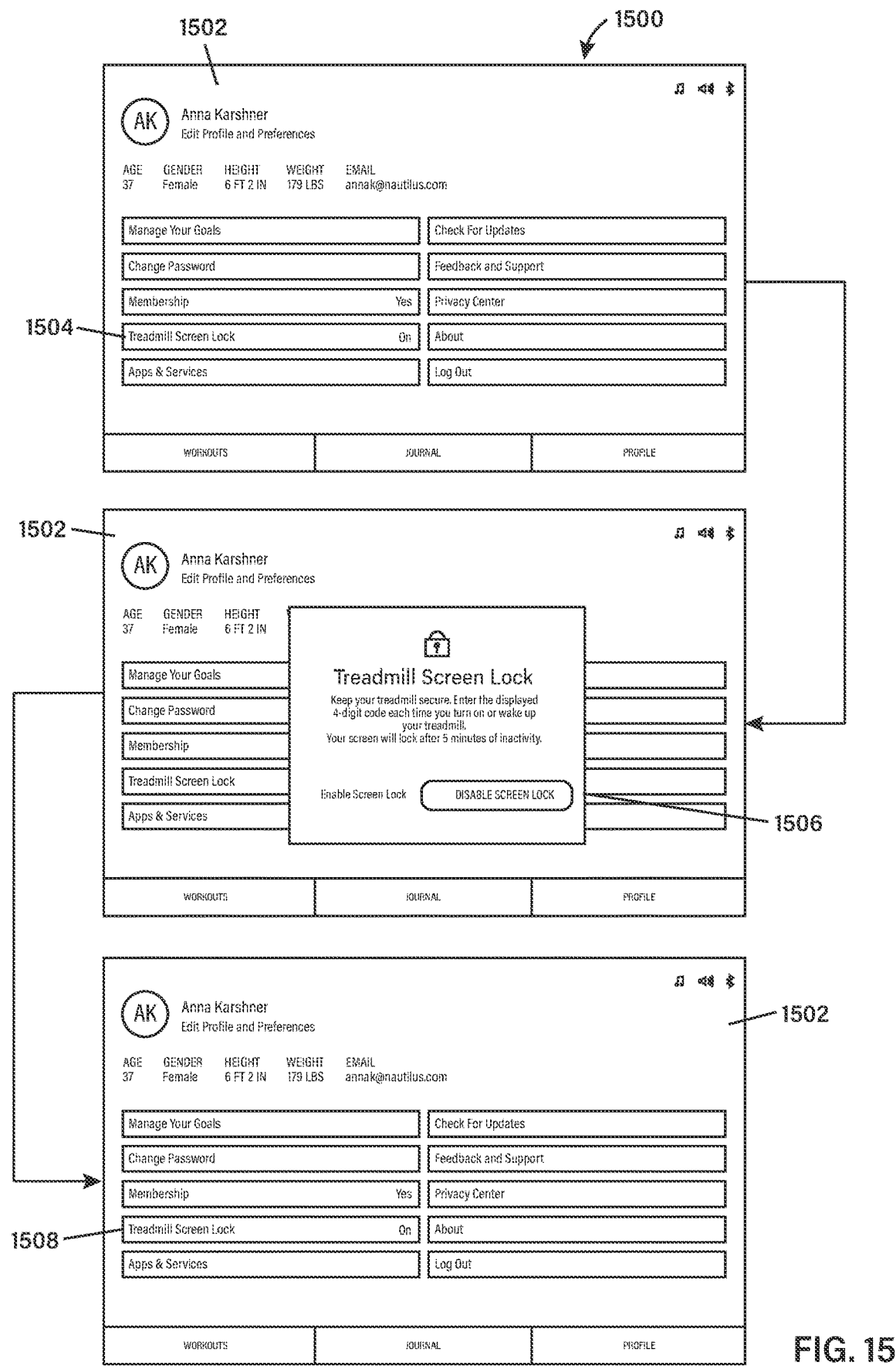
FIG. 15 is a schematic illustration of an example of enabling a screen lock function from user profile settings.

Example 8— Example Method Implementing Enabling Screen Lock Function from Profile Settings FIG. 8 is a sequence diagram illustrating enabling of the screen lock function from profile settings after the user has gained access to the home screen view of the exercise machine (also, see FIG. 15). The screen views generator 102 requests 800 the status of the screen lock function for the user from the screen lock manager 108. The screen lock manager 108 requests 802 the user preferences data 110. The screen lock manager 108 receives 803 the user preferences data 110 and determines if the screen lock function has been enabled for the user. In Example 8, it is assumed that the user has not enabled the screen lock function. Therefore, the screen lock manager 108 requests 804 the screen views generator 102 to show a disabled state for the screen lock function in the profile settings screen.

Subsequently, the user indicates a desire to enable the screen lock function (e.g., by selecting or toggling a button) in the profile settings screen. The screen views generator 102 detects 806 the selection by the user to enable the screen lock function. The screen lock manager 108 receives a request 810 to enable the screen lock function. The screen lock manager 108 requests 812 the screen views generator 102 to generate a screen lock view with a pin code (see Example 5). The screen views generator 102 detects 814 a code entered by the user in the screen lock view. The screen lock manager 108 receives 816 the code entered by the user and compares the code to the pin code used in generating the screen lock view. If the code entered by the user matches the pin code, the screen lock manager 108 updates 818 the user preferences data 110 with information that the screen lock function has been enabled by the user. If the code entered by the user does not match the pin code, the screen lock manager 108 requests 820 the screen views generator 102 to re-prompt the user for a valid pin code.

Figure 9:
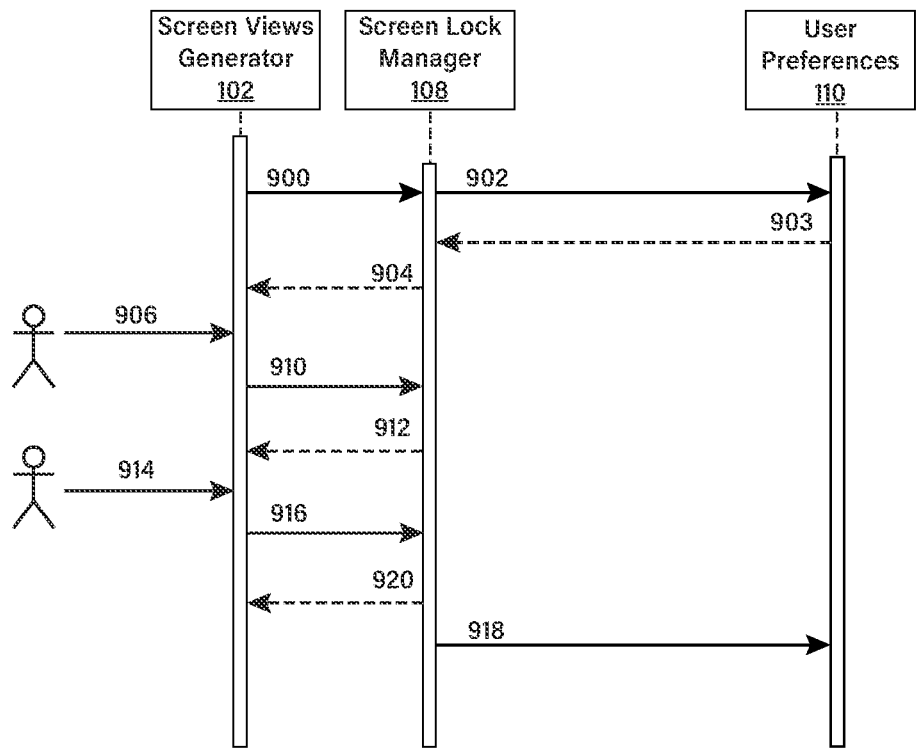
FIG. 9 is a sequence diagram illustrating disabling a screen lock function of an exercise machine from profile settings, according to one example.
Figure 10A:
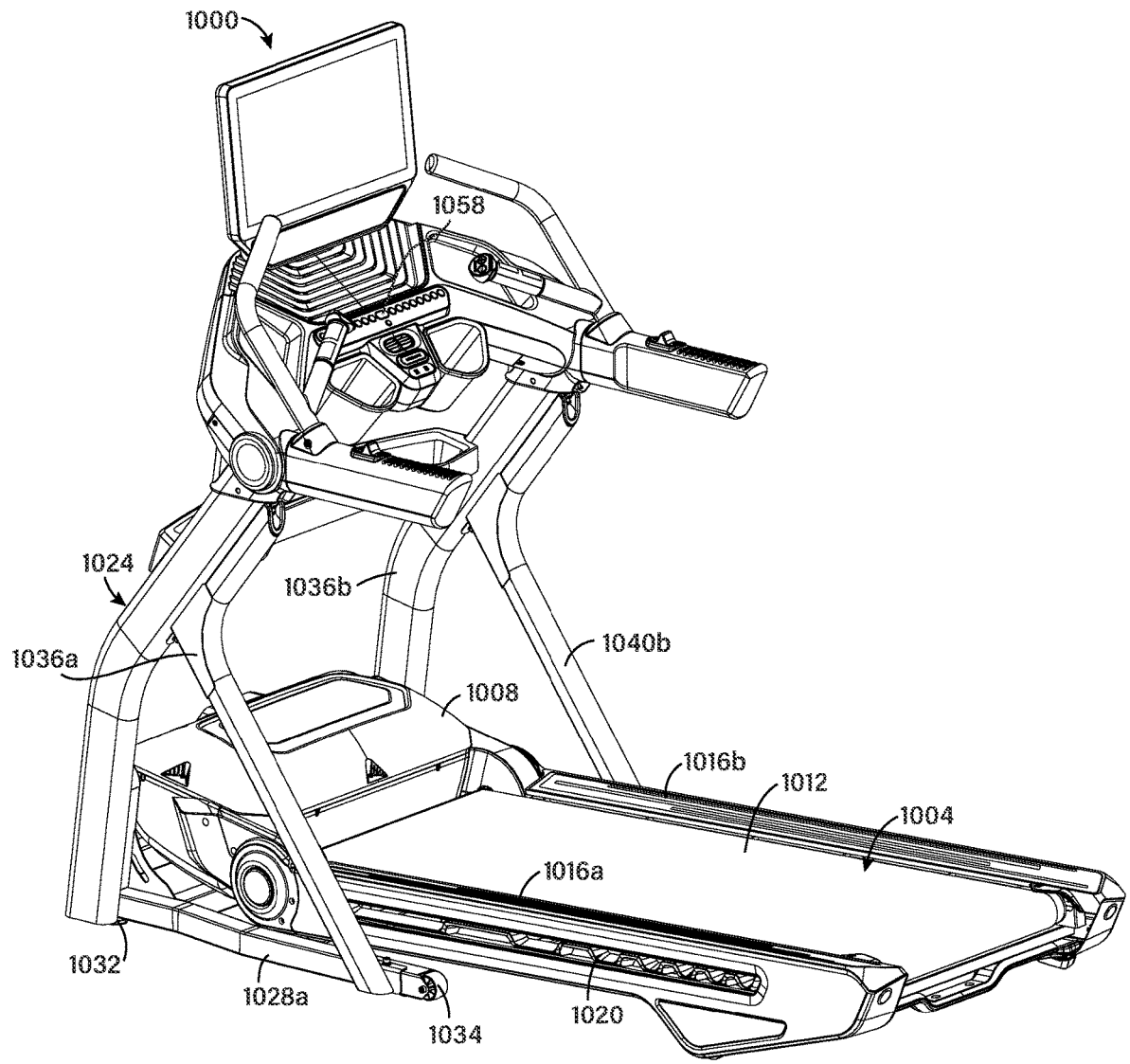
FIGS. 10A-10D illustrate a treadmill implementing a screen lock function, according to one example.
Figure 10B:
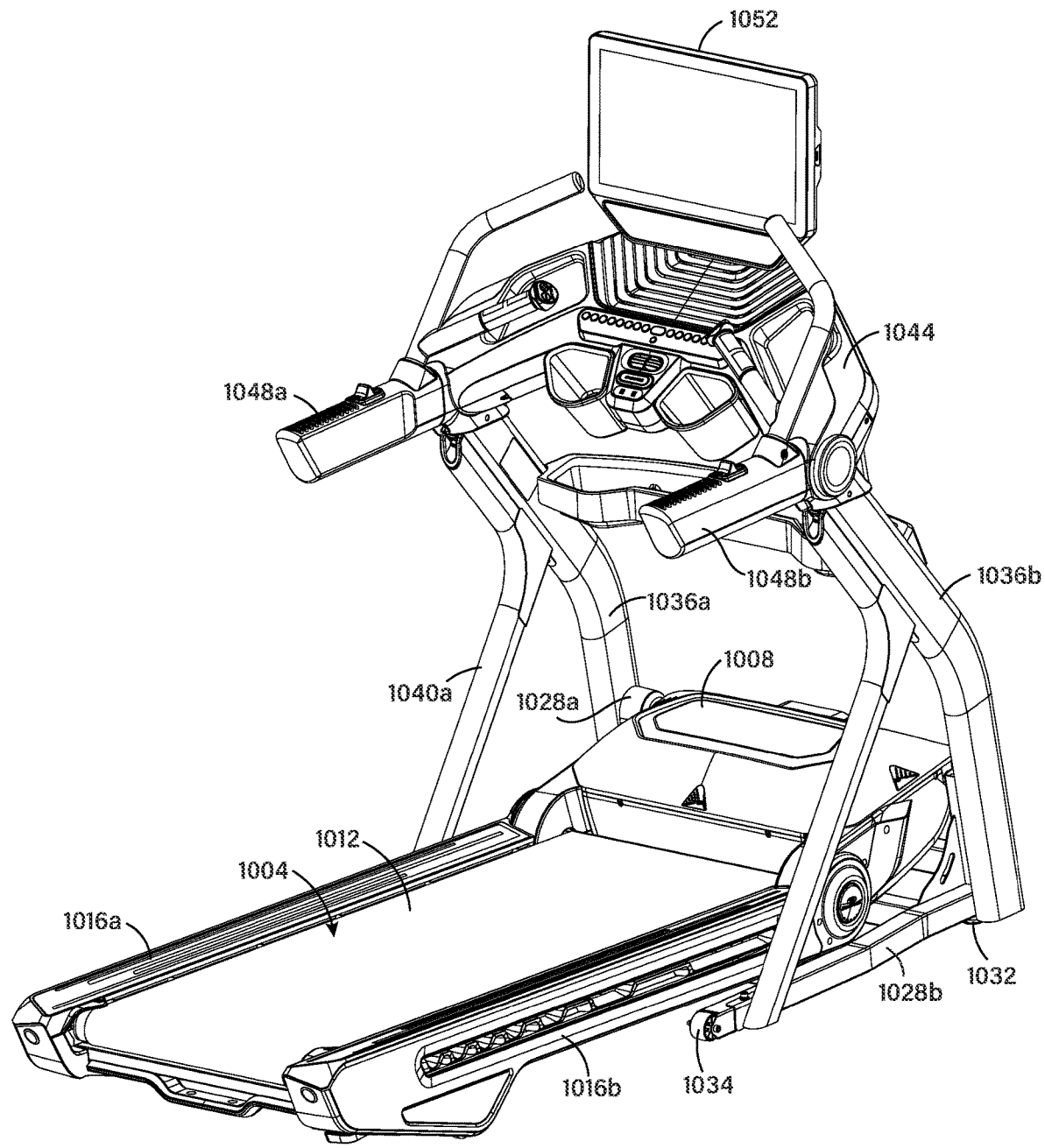
Figure 10C:
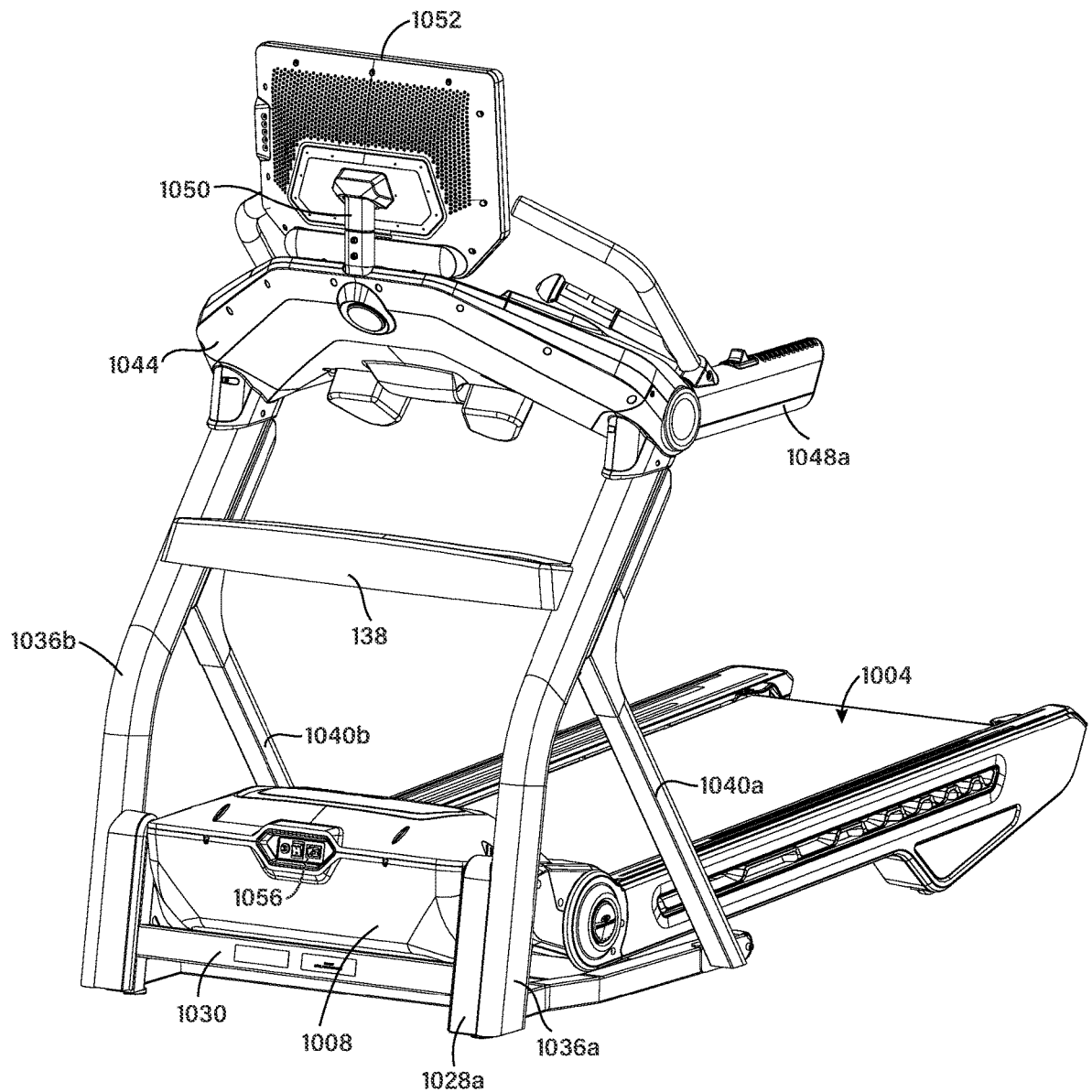
Figure 10D:
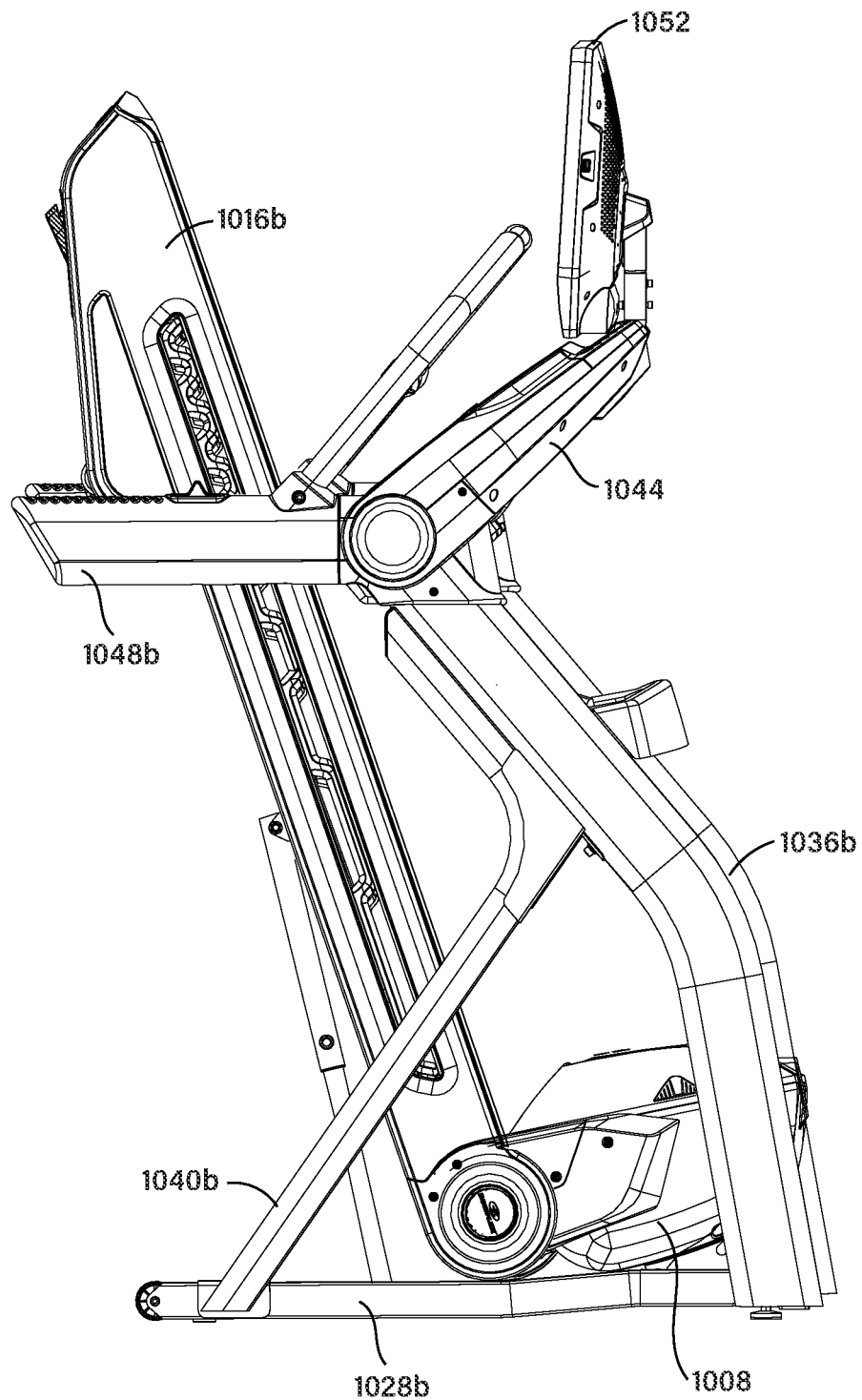
Figure 14:
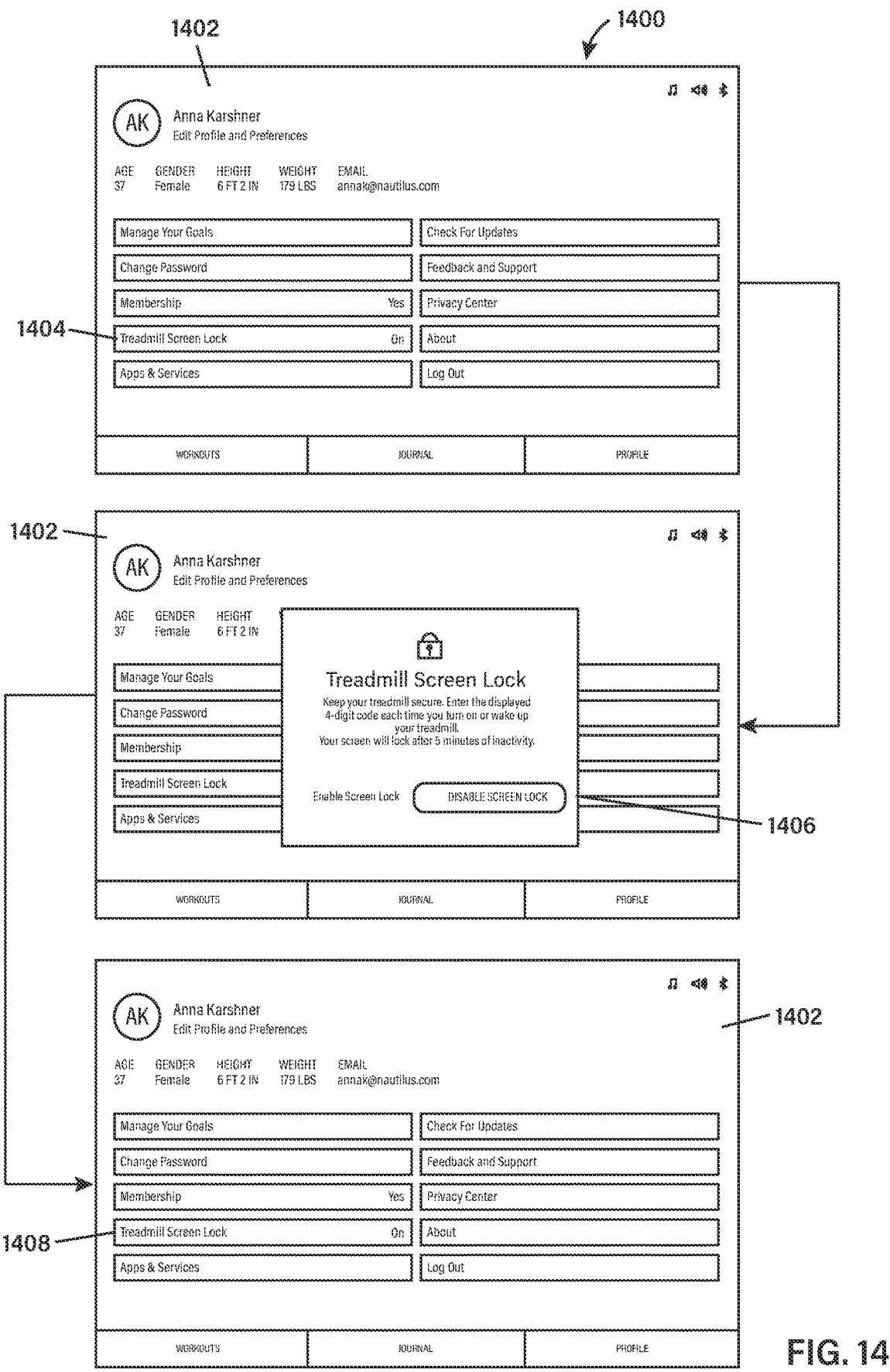
FIG. 14 is a schematic illustration of an example of disabling a screen lock function from user profile settings.

Example 9— Example Method Implementing Disabling Screen Lock Function from Profile Settings FIG. 9 is a sequence diagram illustrating disabling of the screen lock function from profile settings after the user has gained access to the home screen view of the exercise machine (also, see FIG. 14). The user accesses profile settings through the application UI. The screen views generator 102 requests 900 the status of the screen lock function for the user from the screen lock manager 108. The screen lock manager 108 requests 902 the user preferences data 110. The screen lock manager 108 receives 903 the user preferences data 110 and determines if the screen lock function is enabled for the user. In Example 8, the screen lock function is enabled for the user. Therefore, the screen lock manager 108 requests 904 the screen views generator 102 to show an enabled state for the screen lock function in the profile settings screen.

Subsequently, the user indicates a desire to disable the screen lock function (e.g., by selecting or toggling a button) in the profile settings screen. The screen views generator 102 detects 906 the selection by the user to disable the screen lock function. The screen lock manager 108 receives a request 910 to disable the screen lock function. The screen lock manager 108 requests 912 the screen views generator 102 to generate a screen lock view with a pin code (see Example 5). The screen views generator 102 detects 914 a code entered by the user in the screen lock view. The screen lock manager 108 receives 916 the code entered by the user and compares the code to the pin code used in generating the screen lock view. If the code entered by the user matches the pin code, the screen lock manager 108 updates 918 the user preferences data 110 with information that the screen lock function has been disabled by the user. If the code entered by the user does not match the pin code, the screen lock manager 108 requests 920 the screen views generator 102 to re-prompt the user for a valid pin code.

Example 10— Example Screen Lock Function Implementation

The screen lock function can be implemented in any exercise equipment comprising an element actuated by a motor. For example, a treadmill can include a motorized treading belt.

The screen lock function can similarly be implemented in exercise equipment that comprises a motorized incline. Other examples are possible.

When the screen lock is on, the one or more motors of the exercise equipment are off (e.g., the belt is motionless, the incline is not functional, or the like).

The screen lock can thus prevent a moving element from being engaged. In this way, inadvertent startup of the equipment can be avoided.

The screen lock interface can be presented on the exercise equipment itself or on a device (e.g., tablet, phone, or the like) that is associated with the exercise equipment (e.g., via pairing, installing an application, or the like).

Example 11— Example Treadmill Implementing Screen Lock Function

FIGS. 10A-10D illustrate an example treadmill 1000 that can implement the screen lock function in Examples 1-10. The treadmill 1000 is shown in an operating configuration in FIGS. 10A-10C and in a storage configuration in FIG. 10D. The treadmill 1000 can include a deck assembly 1004 pivotally coupled to a housing of an electronics unit 1008. The deck assembly 1004 can include a treading belt and deck 1012 supported between a pair of side foot support rails 1016*a*, 1016*b*. As an example, the treading belt and deck 1012 can be supported on rollers that engage the side foot support rails 1016*a*, 1016*b*. The electronics unit 1008 includes an electrical motor that drives the treading belt and deck 1012. For example, the motor can rotate the rollers in order to propel the treading belt and deck 1012. In some cases, the deck assembly 1004 can include a dampener 1020 to prevent vibrations of the treading belt and deck 1012 while the treading belt and deck 1012 is in motion.

The treadmill 1000 includes a frame assembly 1024 having base members 1028*a*, 1028*b*. The base members 1028a, 1028b have vertical and horizontal portions, with a support bar 1030 extending between and connected to the vertical portions. The horizontal portions of the base members 1028a, 1028b rest on a support surface (such as a ground or floor) and provide a foundational support for the treadmill when the treadmill 1000 in the operating and storage configurations. Levelers 1032 can be attached to the base members 1028a, 1028b to allow leveling of the treadmill 1000 if the support surface is uneven. Transport wheels 1034 can be attached to the base members 1028a, 1028b to facilitate transport of the treadmill 1000 in the storage configuration.

The electronics unit 1008 is disposed between the base members 1028a, 1028b and attached to the vertical portions of the base members 1028a, 1028b. The pivotal connection between the deck assembly 1004 and the housing of the electronics unit 1008 allows the deck assembly 1004 to be rotated between the operating configuration (shown in FIGS. 10A-10C), where the deck assembly 1004 is generally horizontal relative to a support surface, and the storage configuration (shown in FIG. 10D), where the deck assembly is generally vertical relative to the support surface. The pivotal connection can also allow tilting of the deck assembly 1004 to a select inclination relative to the support surface when the treadmill 1000 is in the operating configuration.

The frame assembly 1024 includes upright members 1036a, 1036b, which are attached to the base members 1028a, 1028b and extend upwardly from the base members 1028a, 1028b. A crossbar 138 extends between and is connected to the upright members 1036a, 1036b, improving the structural strength of the frame assembly 1024. Upright supports 1040a, 1040b in the form of braces can extend between and connect the upright members 1036a, 1036b and the base members 1028a, 1028b, further improving the structural integrity of the frame assembly 1024.

The treadmill 1000 can include a console base assembly 1044 mounted on the upright members 1036a, 1036b. Handlebars 1048a, 1048b can be attached to the console base assembly 1044 and can extend generally parallel to the deck assembly 1004 when the treadmill 1000 is in the operating condition. A console mast 1050 can be attached to the top of the console base assembly 1044. The console mast 1050 can support a console 1052 with a display. Electrical and communication connections can be made between the console 1052 and electronics unit 1008 through cables that pass from the console 1052, through the console mast 1050, console base assembly 1044, and upright members 1036a, 1036b, to the electronics unit 1008, which can be connected to a power source via an electrical port 1056.

Further details of the treadmill can be found in, for example, U.S. Pat. No. 10,398,932, which is incorporated herein by reference.

The console 1052 can run a machine application as described in Example 1, which can implement a screen lock function to control access to the treadmill as described in Examples 2-10. The control base assembly 1044 can include a start button 1058 and various other control buttons to control the speed and/or inclination of the treadmill. While the treadmill is screen locked, communication between the start button and control button and the electronics unit 1008 can be blocked by the machine application, thereby preventing motorized functions of the treadmill from working. After the user unlocks the treadmill, the user can select a workout configuration from the machine application UI and start the workout (e.g., using the start button 1058).

The machine application can be configured such that when the treadmill is idle for a predetermined amount of time, the treadmill is screen locked. The predetermined period can be based on whether the user has a paused workout or no workout. For example, the predetermined period can be shorter (e.g., 5 minutes) when there is no workout selected on the treadmill and can be relatively longer (e.g., between 6 minutes and 60 minutes) when there is a paused workout. In other cases, the treadmill can have sensors to detect weight on the treading belt and deck 1012 and can lock the treadmill when the weight is below a certain threshold.

Example 12— Treadmill Screen Lock Features

The screen lock function for the treadmill can have one or more of the following features.

The screen lock helps prevent unintentionally turning on the treadmill.

The screen lock function has an opt out function so that the user can reduce the number of steps to start a workout. The opt out function can be accessible within the profile of the user. The user can opt-in upon updating or fresh install of a version of the machine application.

The screen lock function can be enabled/disabled for all users if at least one user enables or disables the screen lock function.

The screen lock function can be quickly activated to allow the user to step away quickly from the treadmill.

The screen lock has a code that the user has to enter. The screen lock function can present a new code every time the machine wakes up or the user logs in. The new code can be a random number presented to the user on the screen such that the user can read the number and enter it as a screen lock code. The screen lock function does not require the user to remember this code for further use, nor does it require the user to manage the code.

The screen lock function can be semi-secure, i.e., nothing happens if the user enters a wrong code, and the user can have unlimited failed attempts at entering the code to unlock the screen.

The screen lock function can be engaged automatically if the treadmill is inactive and the screen goes to sleep/dims. This can be 5 minutes or the same time as the screen going to sleep, except in a few cases when the user is within a workout or when pausing a workout. In the case of paused workouts, if the workout has been paused and the screen is dimmed, if it has been less than 60 mins, then the workout should still be able to be un-paused and resumed. In this case, waking the screen from being dimmed would present the screen lock but take the user back into the workout. If it has been more than 60 mins, then the workout should have been automatically ended. In this case, waking the screen from being dimmed would present the screen lock but take the user to the post-workout flow as would be expected post-workout When the screen lock is on, the treadmill belt is off, and the incline is not functional.

Example 13— Example Method Implementing First Time Use of Exercise Machine with Screen Lock Function The first time a user accesses the exercise machine, the machine application can prompt the user to register with the exercise machine. FIG. 11 illustrates an example of a registration prompt 1100 that can be presented to the user on the display 104 (see Example 2). In the example, the user is invited to create a new profile. The registration prompt 1100 asks for a unique confirmation code from the user. The user can enter the unique confirmation code (which can be obtained, for example, from an email sent to the user) in a text area 1103 on the registration prompt and continue the registration by selecting a button 1105 on the registration prompt.

In response to selecting the button 1104, the machine application can determine if the user entered the correct unique confirmation code. If the correct unique confirmation was entered, the machine application can present a screen lock authorization view on the display 104 (for example, using the screen views generator 102 as described in Example 3). FIG. 11 shows an example of a screen lock authorization view 1104 overlaid on an exercise interface 1106 on the display 104. The screen lock authorization view 1104 can include a first selection element 1108 (such as text, button, or image) that the user can select to disable the screen lock function and a second selection element 1110 (such as text, button, or image) that the user can select to enable the screen lock function. The screen lock authorization view 1104 can be in a modal view such that the user cannot interact with the exercise interface 1106 without enabling or disabling the screen lock function. In some examples, the second selection element 1110 that enables the screen lock function can be highlighted to encourage the user to enable the screen lock function.

If the user chooses to enable the screen lock function, the machine application can receive the selection and update the machine configuration data (shown as 112 in FIG. 1) to indicate that the screen lock function is enabled for the exercise machine. On the other hand, if the user chooses not to enable the screen lock function, the machine application can receive the selection and update the machine configuration data to indicate that the screen lock function is disabled for the exercise machine. The preference of the user to enable or disable the screen lock function can be stored in the user profile associated with the user. The user profile can be created as part of registering the user on the exercise machine (for example, after the user successfully enters the unique confirmation code).

Example 14— Example Method Implementing Accessing Training Screen with Screen Lock Function FIG. 12A illustrates a sequence of operations 1200 for accessing a training screen with a screen lock function. In Example 14, a user has registered on the exercise machine but has not enabled or disabled the screen lock function. At 1202, the machine application (for example, using the screen views generator 102 in Example 2) presents a screen lock authorization view 1204 on the display 104 (see Example 2) where the user can choose to disable screen lock or enable screen lock (as described in Example 13). In some examples, the screen lock authorization view 1204 is shown overlaid on a training screen 1206 in modal mode so that the user can see the training screen 1206 but cannot interact with the training screen 1206 until a selection is made on the screen lock authorization view 1204.

If the user enables the screen lock function, the machine application (for example, using the screen views generator 102 in Example 1) then displays a screen lock view 1208, as shown at 1210, on the display 104. In some examples, the screen lock view 1208 can be overlaid on the training screen 1206 in modal mode so that the user can see the training screen 1206 but cannot interact with the training screen until the correct pin code is entered in the screen lock view 1208. The user can enter a pin code in the screen lock view 1204, as shown at 1212 and 1214, for example, using a virtual keypad (as described in Example 5). Herein and in the other examples, the user can submit the pin code by selecting an appropriate button (such as on the virtual keypad), or the pin code can be automatically submitted after the user enters a digit in all the spaces allotted for the pin code.

After the user submits the pin code, the machine application determines if the pin code matches a goal code. In some examples, the goal code is displayed on the screen lock view 1208 (as described in Example 5). If the machine application determines that the pin code entered by the user does not match the goal code, the machine application can display an error message on the screen lock view 1208 and allow the user another opportunity to enter the pin code, as illustrated in FIG. 12B.

If the machine application determines that the pin code entered by the user matches the goal code, as illustrated at 1214 in FIG. 12A, the machine application removes the screen lock view 1204 and allows the user to interact with the training screen 1206, as illustrated at 1216 in FIG. 12A. In some examples, the machine application can additionally trigger a motor of the exercise machine to an enabled state.

Example 15— Example Method Implementing Accessing Home Screen with Screen Lock Function FIG. 13 illustrates a sequence of operations 1300 for accessing a home screen of the machine application with a screen lock function. In Example 15, it is assumed that the screen lock function has been enabled and that the home screen of the machine application is behind a screen lock (or that the screen lock is on).

The user taps on a blank screen 1302 on the display 104 (see Example 2). The screen views generator 102 (see Example 2) detects the tapping and informs the screen lock manager 108 (see Example 2) that a user has tapped the screen. The screen lock manager 108 sends a request to the server for the machine configuration data 112 (see Example 2). The screen lock manager 108 receives the machine configuration data 112 and determines whether the screen lock function has been enabled for the exercise machine.

The screen lock manager 108 determines that the screen lock function has been enabled and requests the screen views generator 102 to present a screen lock view 1304 to the user on the display 104, as shown at 1306. The screen views generator 102 can also present the home screen 1308 of the machine application. In the example, the screen lock authorization view 1304 is overlaid on the home screen 1308. The screen lock view 1304 can be in modal mode such that the user cannot interact with the home screen 1308 until the screen lock view 1304 is dismissed.

The user can enter a pin code in the screen lock view 1304, as shown at 1310, for example, using a virtual keypad (as described in Example 5). After the user submits the pin code, the machine application determines if the pin code matches a goal code. In some examples, the goal code is displayed on the screen lock view 1304 (as described in Example 5) and the user simply needs to enter the displayed goal code as the pin code. If the machine application determines that the pin code entered by the user matches the goal code, the machine application removes the screen lock view 1304 and allows the user to interact with the home screen 1308, as illustrated at 1312. In some examples, the machine application can additionally trigger a motor of the exercise machine to an enabled state.

Example 16— Example Method Implementing Disabling Screen Lock Function

FIG. 14 illustrates a sequence of operations 1400 for disabling a screen lock function on an exercise machine after it has been previously enabled. A user can cause a user profile screen 1402 to be presented on the display 104 (see Example 2) by selecting an appropriate menu item from the training screen or home screen (see Examples 14 and 15) of the machine application user interface. From the user profile screen 1402, the user can select a screen lock option 1404. Upon selecting the screen lock option 1404, the machine application can present a screen lock authorization view 1406 on the display 104, for example, overlaid on the user profile screen 1402. The user can disable the screen lock function from the screen lock authorization view 1406. After the user makes a selection on the screen lock authorization view 1406, the screen lock function option on the user profile screen 1402 can be updated with the selection, as shown at 1408.

In some examples, after the user disables the screen lock function via the user profile screen, the screen lock function is disabled for all the users on the exercise machine. In other examples, the changes made via the user profile screen only applies to the user making the changes.

Example 17— Example Method Implementing Enabling Screen Lock Function

FIG. 15 illustrates a sequence of operations 1500 for enabling a screen lock function on an exercise machine after it has been previously enabled. A user can cause a user profile screen 1502 to be presented on the display 104 (see Example 2) by selecting an appropriate menu item from the training screen or home screen (see Examples 14 and 15) of the machine application user interface. From the user profile screen 1502, the user can select a screen lock option 1504. Upon selecting the screen lock option 1504, the machine application can present a screen lock authorization view 1506 on the display 104, for example, overlaid on the user profile screen 1502. The user can enable the screen lock function from the screen lock authorization view 1506. After the user makes a selection on the screen lock authorization view 1506, the screen lock option on the user profile screen 1502 can be updated with the selection, as shown at 1508.

In some examples, after the user enables the screen lock function via the user profile screen, the screen lock function is enabled for all the users on the exercise machine. In other examples, the changes made via the user profile screen only applies to the user making the changes.

Advantages

In the various examples, the digits of the goal code are displayed to the user alongside the screen lock view or on the screen lock view. Even though the digits of the goal code are displayed with the screen lock view, allowing easy activation by a user who can read digits, persons who are too young to recognize digits (e.g., a very young child or pets) cannot easily activate the exercise machine.

Example Computing Systems

Figure 16:
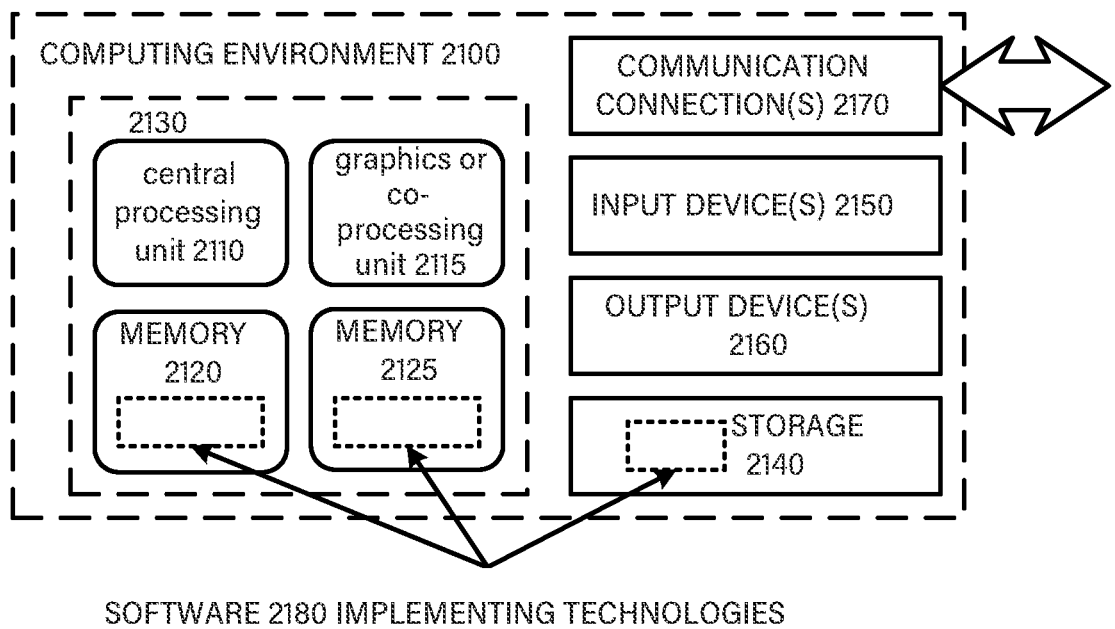
FIG. 16 is a block diagram of an example computing system in which described embodiments can be implemented.

FIG. 16 depicts an example of a suitable computing system 2100 in which the described innovations can be implemented. The computing system 2100 is not intended to suggest any limitation as to scope of use or functionality of the present disclosure, as the innovations can be implemented in diverse computing systems.

With reference to FIG. 16, the computing system 2100 includes one or more processing units 2110, 2115 and memory 2120, 2125. In FIG. 16, this basic configuration 2130 is included within a dashed line. The processing units 2110, 2115 execute computer-executable instructions, such as for implementing the features described in the examples herein. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 16 shows a central processing unit 2110 as well as a graphics processing unit or co-processing unit 2115. The tangible memory 2120, 2125 can be volatile memory (e.g., registers, cache, RAM), non-volatile memory (e.g., ROM, EEPROM, flash memory, etc.), or some combination of the two, accessible by the processing unit(s) 2110, 2115. The memory 2120, 2125 stores software 2180 implementing one or more innovations described herein, in the form of computer-executable instructions suitable for execution by the processing unit(s) 2110, 2115.

A computing system 2100 can have additional features. For example, the computing system 2100 includes storage 2140, one or more input devices 2150, one or more output devices 2160, and one or more communication connections 2170, including input devices, output devices, and communication connections for interacting with a user. An interconnection mechanism (not shown) such as a bus, controller, or network interconnects the components of the computing system 2100. Typically, operating system software (not shown) provides an operating environment for other software executing in the computing system 2100, and coordinates activities of the components of the computing system 2100.

The tangible storage 2140 can be removable or non-removable, and includes magnetic disks, magnetic tapes or cassettes, CD-ROMs, DVDs, or any other medium which can be used to store information in a non-transitory way and which can be accessed within the computing system 2100. The storage 2140 stores instructions for the software 2180 implementing one or more innovations described herein.

The input device(s) 2150 can be an input device such as a keyboard, mouse, pen, or trackball, a voice input device, a scanning device, touch device (e.g., touchpad, display, or the like) or another device that provides input to the computing system 2100. The output device(s) 2160 can be a display, printer, speaker, CD-writer, or another device that provides output from the computing system 2100.

The communication connection(s) 2170 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the context of computer-executable instructions, such as those included in program modules, being executed in a computing system on a target real or virtual processor (e.g., which is ultimately executed on one or more hardware processors). Generally, program modules or components include routines, programs, libraries, objects, classes, components, data structures, etc. that perform particular tasks or implement particular abstract data types. The functionality of the program modules can be combined or split between program modules as desired in various embodiments. Computer-executable instructions for program modules can be executed within a local or distributed computing system.

For the sake of presentation, the detailed description uses terms like "determine" and "use" to describe computer operations in a computing system. These terms are high-level descriptions for operations performed by a computer and should not be confused with acts performed by a human being. The actual computer operations corresponding to these terms vary depending on implementation.

Computer-Readable Media

Any of the computer-readable media herein can be non-transitory (e.g., volatile memory such as DRAM or SRAM, nonvolatile memory such as magnetic storage, optical storage, or the like) and/or tangible. Any of the storing actions described herein can be implemented by storing in one or more computer-readable media (e.g., computer-readable storage media or other tangible media). Any of the things (e.g., data created and used during implementation) described as stored can be stored in one or more computer-readable media (e.g., computer-readable storage media or other tangible media). Computer-readable media can be limited to implementations not consisting of a signal.

Any of the methods described herein can be implemented by computer-executable instructions in (e.g., stored on, encoded on, or the like) one or more computer-readable media (e.g., computer-readable storage media or other tangible media) or one or more computer-readable storage devices (e.g., memory, magnetic storage, optical storage, or the like). Such instructions can cause a computing system to perform the method. The technologies described herein can be implemented in a variety of programming languages.

Example Cloud Computing Environment

Figure 17:
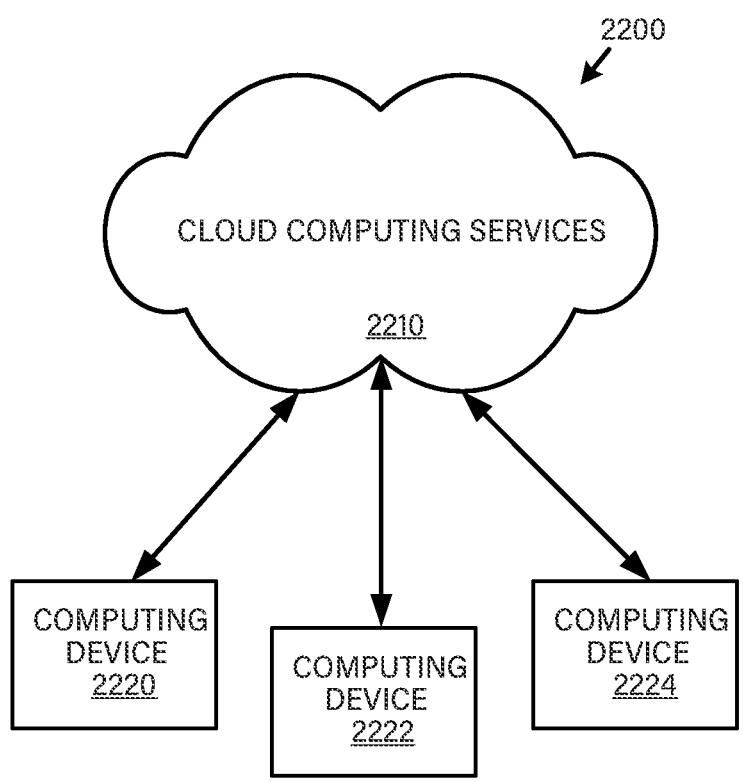
FIG. 17 is a block diagram of an example cloud computing environment that can be used in conjunction with the technologies described herein.

FIG. 17 depicts an example cloud computing environment 2200 in which the described technologies can be implemented, including, e.g., the systems described systems herein. The cloud computing environment 2200 comprises cloud computing services 2210. The cloud computing services 2210 can comprise various types of cloud computing resources, such as computer servers, data storage repositories, networking resources, etc. The cloud computing services 2210 can be centrally located (e.g., provided by a data center of a business or organization) or distributed (e.g., provided by various computing resources located at different locations, such as different data centers and/or located in different cities or countries).

The cloud computing services 2210 are utilized by various types of computing devices (e.g., client computing devices), such as computing devices 2220, 2222, and 2224. For example, the computing devices (e.g., 2220, 2222, and 2224) can be computers (e.g., desktop or laptop computers), mobile devices (e.g., tablet computers or smart phones), or other types of computing devices. For example, the computing devices (e.g., 2220, 2222, and 2224) can utilize the cloud computing services 2210 to perform computing operations (e.g., data processing, data storage, and the like).

In practice, cloud-based, on-premises-based, or hybrid scenarios can be supported.

Additional Examples

Additional examples based on principles described herein are enumerated below. Further examples falling within the scope of the subject matter can be configured by, for example, taking one feature of an example in isolation, taking more than one feature of an example in combination, or combining one or more features of one example with one or more features of one or more other examples.

Example 1: A system comprises an exercise machine having a lock mode and an unlock mode associated with a screen lock function and a computing device coupled to the exercise machine. The computing device comprises a display, memory, and a processor coupled to the memory, wherein the memory stores instructions that when executed by the processor causes the computing device to perform operations comprising: detecting a user interaction with the computing device or the exercise machine while the exercise machine is in the lock mode; rendering a screen lock interface on the display in response to the user interaction; receiving an input code from the screen lock interface; determining that the input code matches a goal code; and adjusting the exercise machine from the lock mode to the unlock mode in response to determining that the input code matches the goal code.

Example 2: A system according to Example 1, wherein the exercise machine comprises a movable element actuated by a motor, and wherein the motor is in a disabled state when the exercise machine is in the lock mode.

Example 3: A system according to Example 2, wherein the movable element comprises a treadmill belt.

Example 4: A system according to any one of Examples 1 to 3, wherein the computing device is a console attached to the exercise machine.

Example 5: A system according to any one of Examples 1 to 3, wherein the computing device is a portable device communicatively coupled to the exercise machine.

Example 6: A system according to any one of Examples 1 to 5, wherein the operations comprise presenting the goal code on the display in response to the user interaction.

Example 7: A system according to any one of Examples 1 to 6, wherein the operations comprise presenting the goal code on the display concurrently with rendering the screen lock interface on the display.

Example 8: A method of operating an exercise machine comprises detecting a user interaction with an exercise machine or a computing device coupled to the exercise machine while the exercise machine is in a lock mode associated with a screen lock function; presenting a screen lock interface on a display of the computing device; receiving an input code from the screen lock interface; determining that the input code matches a goal code; and adjusting the exercise machine from the lock mode to an unlock mode in response to determining that the input code matches the goal code.

Example 9: A method according to Example 8, wherein detecting the user interaction comprises detecting a touch interaction with the display of the computing device.

Example 10: A method according to any one of Examples 8 to 9, further comprising presenting the goal code on the display.

Example 11: A method according to Example 10, wherein presenting the goal code is simultaneous with presenting the screen lock interface.

Example 12: A method according to Example 10, wherein presenting the goal code on the display comprises randomly generating the goal code.

Example 13: A method according to any one of Examples 8 to 9, further comprising generating the goal code and presenting the goal code on the display while the goal code is generated.

Example 14: A method according to any one of Examples 8 to 9, further comprising receiving a request for the goal code from the screen lock interface and presenting the goal code on the display.

Example 15: A method according to any one of claims 8 to 14, wherein adjusting the exercise machine to the unlock mode comprises adjusting a motor of the exercise machine from a disabled state to an enabled state.

Example 16: A method according to any one of claims 8 to 15, further comprising detecting a user identifier from the user interaction; determining that a screen lock function for the user identifier is not enabled; and presenting a screen lock authorization interface on the display of the computing device.

Example 17: A method according to Example 16, further comprising receiving a screen lock preference from the screen lock authorization interface; and storing the screen lock preference in association with the user identifier.

Example 18: A method according to Example 17, wherein the screen lock preference disables the screen lock function, and further comprising updating the screen lock preference for a set of user identifiers associated with the exercise machine to disable the screen lock function.

Example 19: A method according to Example 17, wherein the screen lock preference disables the screen lock function, and further comprising requesting a machine configuration of the exercise machine from a server; and updating the machine configuration data to disable the screen lock function for the exercise machine.

Example 20: A method according to any one of Examples 8 to 14, further comprising, in response to detecting the user interaction, requesting a machine configuration of the exercise machine from a server; and determining that a screen lock function for the exercise machine is enabled from the machine configuration prior to presenting a screen lock interface on the display.

Example 21: A method according to any one of Examples 8 to 20, further comprising detecting that the exercise machine is idle for a select time period; and adjusting the exercise machine from the unlock mode to the lock mode.

Example 22: One or more non-transitory computer-readable media comprising computer-executable instructions that when executed cause a computing system to perform operations comprising: detecting a user interaction with an exercise machine or a computing device coupled to the exercise machine while the exercise machine is in a lock mode associated with a screen lock function; presenting a screen lock interface on a display of the computing device, the screen lock interface comprising a goal code; receiving an input code from the screen lock interface; determining that the input code matches the goal code; and adjusting the exercise machine from the lock mode to an unlock mode in response to determining that the input code matches the goal code.

EXAMPLE IMPLEMENTATIONS

Although the operations of some of the disclosed methods are described in a particular, sequential order for convenient presentation, such manner of description encompasses rearrangement, unless a particular ordering is required by specific language set forth herein. For example, operations described sequentially can in some cases be rearranged or performed concurrently.
Alternatives The technologies from any example can be combined with the technologies described in any one or more of the other examples. In view of the many possible embodiments to which the principles of the disclosed technology can be applied, it should be recognized that the illustrated embodiments are examples of the disclosed technology and should not be taken as a limitation on the scope of the disclosed technology. Rather, the scope of the disclosed technology includes what is covered by the scope and spirit of the claims.

The invention claimed is:

1. A system comprising:
   an exercise machine having a lock mode and an unlock mode associated with a screen lock function; and
   a computing device coupled to the exercise machine, the computing device comprising a display, memory, and a processor coupled to the memory, wherein the memory stores instructions that when executed by the processor causes the computing device to perform operations comprising:
   detecting a user interaction with the computing device or the exercise machine while the exercise machine is in the lock mode;
   rendering a screen lock interface on the display in response to the user interaction;
   receiving an input code from the screen lock interface;
   determining that the input code matches a goal code;
   adjusting the exercise machine from the lock mode to the unlock mode in response to determining that the input code matches the goal code;
   detecting a user identifier from the user interaction;
   determining that a screen lock function for the user identifier is not enabled;
   presenting a screen lock authorization interface on the display of the computing device;
   receiving a screen lock preference from the screen lock authorization interface;
   disabling the screen lock function based on the screen lock preference; and
   updating the screen lock preference for a set of user identifiers associated with the exercise machine to disable the screen lock function.

2. The system of claim 1, wherein the exercise machine comprises a movable element actuated by a motor, and wherein the motor is in a disabled state when the exercise machine is in the lock mode.

3. The system of claim 2, wherein the movable element comprises a treadmill belt.

4. The system of claim 1, wherein the computing device is a console attached to the exercise machine.

5. The system of claim 1, wherein the operations comprise presenting the goal code on the display in response to the user interaction.

6. The system of claim 1, wherein the operations comprise presenting the goal code on the display concurrently with rendering the screen lock interface on the display.

7. A method of operating an exercise machine, the method comprising:
   detecting a user interaction with an exercise machine or a computing device coupled to the exercise machine while the exercise machine is in a lock mode associated with a screen lock function;
   presenting a screen lock interface on a display of the computing device;
   receiving an input code from the screen lock interface;
   determining that the input code matches a goal code;
   adjusting the exercise machine from the lock mode to an unlock mode in response to determining that the input code matches the goal code;

detecting a user identifier from the user interaction;
determining that a screen lock function for the user identifier is not enabled;
presenting a screen lock authorization interface on the display of the computing device;
receiving a screen lock preference from the screen lock authorization interface;
disabling the screen lock function based on the screen lock preference; and
updating the screen lock preference for a set of user identifiers associated with the exercise machine to disable the screen lock function.

8. The method of claim 7, wherein detecting the user interaction comprises detecting a touch interaction with the display of the computing device.

9. The method of claim 7, further comprising presenting the goal code on the display.

10. The method of claim 9, wherein presenting the goal code is simultaneous with presenting the screen lock interface.

11. The method of claim 9, wherein presenting the goal code on the display comprises randomly generating the goal code.

12. The method of claim 9, further comprising generating the goal code and presenting the goal code on the display while the goal code is generated.

13. The method of claim 7, further comprising receiving a request for the goal code from the screen lock interface and presenting the goal code on the display.

14. The method of claim 7, wherein adjusting the exercise machine to the unlock mode comprises adjusting a motor of the exercise machine from a disabled state to an enabled state.

15. The method of claim 7, further comprising:
storing the screen lock preference in association with the user identifier.

16. The method of claim 7, further comprising:
requesting a machine configuration data of the exercise machine from a server; and
updating the machine configuration data to disable the screen lock function for the exercise machine.

17. The method of claim 7, further comprising:
detecting that the exercise machine is idle for a select time period; and
adjusting the exercise machine from the unlock mode to the lock mode.

18. One or more non-transitory computer-readable media comprising computer-executable instructions that when executed cause a computing system to perform operations comprising:
detecting a user interaction with an exercise machine or a computing device coupled to the exercise machine while the exercise machine is in a lock mode associated with a screen lock function;
presenting a screen lock interface on a display of the computing device, the screen lock interface comprising a goal code;
receiving an input code from the screen lock interface;
determining that the input code matches the goal code;
adjusting the exercise machine from the lock mode to an unlock mode in response to determining that the input code matches the goal code;
detecting a user identifier from the user interaction;
determining that a screen lock function for the user identifier is not enabled;
presenting a screen lock authorization interface on the display of the computing device;
receiving a screen lock preference from the screen lock authorization interface;
disabling the screen lock function based on the screen lock preference; and
updating the screen lock preference for a set of user identifiers associated with the exercise machine to disable the screen lock function.

* * * * *